(12) United States Patent
Brookes

(10) Patent No.: US 8,247,172 B2
(45) Date of Patent: Aug. 21, 2012

(54) HIGH MULIPLEX NUCLEIC ACID AMPLIFICATION

(75) Inventor: Anthony Joseph Brookes, Leicester (GB)

(73) Assignee: University of Leicester, Leicester (GB)

( * ) Notice: Subject to any disclaimer, the term of this patent is extended or adjusted under 35 U.S.C. 154(b) by 237 days.

(21) Appl. No.: 12/665,900

(22) PCT Filed: Jul. 3, 2008

(86) PCT No.: PCT/GB2008/002273
§ 371 (c)(1),
(2), (4) Date: Dec. 21, 2009

(87) PCT Pub. No.: WO2009/004335
PCT Pub. Date: Jan. 8, 2009

(65) Prior Publication Data
US 2010/0184153 A1 Jul. 22, 2010

(30) Foreign Application Priority Data
Jul. 3, 2007 (GB) .................................. 0712882.0

(51) Int. Cl.
*C12Q 1/68* (2006.01)
*C12P 19/34* (2006.01)
*C07H 21/02* (2006.01)
*C07H 21/04* (2006.01)

(52) U.S. Cl. ....... 435/6.1; 435/91.2; 536/23.1; 536/24.3

(58) Field of Classification Search .................. None
See application file for complete search history.

(56) References Cited

U.S. PATENT DOCUMENTS

| | | | | |
|---|---|---|---|---|
| 5,712,386 A | * | 1/1998 | Wang et al. | 536/24.33 |
| 6,033,851 A | * | 3/2000 | Yamane | 435/6.18 |
| 6,274,351 B1 | | 8/2001 | Peponnet | |
| 2006/0057571 A1 | | 3/2006 | Repp | |

FOREIGN PATENT DOCUMENTS

WO WO-2005/071078 A1 8/2005

OTHER PUBLICATIONS

Adessi et al. (2000) "Solid phase DNA amplification: characterization of primer attachment and amplification mechanisms," *Nucleic Acids Research* 28(20): e87, 8 pages.

Broude et al. (2001) "Multiplex allele-specific target amplification based on PCR suppression," *PNAS* 98(1): 206-211.

Dahl et al. (2005) "Multiplex amplification enabled by selective circularization of large sets of genomic DNA fragments," *Nucleic Acids Research* 33(8):e71, 7 pages.

(Continued)

*Primary Examiner* — Teresa E Strzelecka
(74) *Attorney, Agent, or Firm* — Goodwin Procter LLP

(57) ABSTRACT

This invention relates to the amplification of multiple nucleic acid target sequences. Forward and reverse compound primers comprising a common amplification sequence and a target-specific primer sequence are immobilized at a site on a solid support. Target regions of single-stranded template DNA are primed and copied by the forward primer to produce a first extension product. The template DNA is removed and the first extension product is primed and copied by the reverse primer to produce a second extension product. The second extension product has common amplification sequences at each end and is bulk-amplified in solution by regular PCR employing primers that target the common amplification sequences. These methods allow highly multiplexed amplifications to be performed.

10 Claims, 6 Drawing Sheets

OTHER PUBLICATIONS

Li et al. (1996) "Multiplex co-amplification of 24 retinoblastoma gene exons after pre-amplification by long-distance PCR," *Nucleic Acids Research* 24(3): 538-539.

Lin et al. (1996) "Multiplex genotype determination at a large number of gene loci" *PNAS* 93:.2582-2587.

Shapero et al. (2004) "MARA: a novel approach for highly multiplexed locus-specific SNP genotyping using high-density DNA oligonucleotide arrays," *Nucleic Acids Research* 32(22): e181, 9 pages.

Tillib et al. (2001) "Integration of Multiple PCR Amplifications and DNA Mutation Analyses by Using Oligonucleotide Microchip," *Analytical Biochemistry* 292(1): 155-160.

Pemov et al.(2005) "DNA analysis with multiplex microarray-enhanced PCR," *Nucleic Acids Research* 33(2):e11, 9 pages.

Meuzelaar et al.(2007) "MegaPlex PCR: a strategy for multiplex amplification," *Nature Methods* 4(10):835-837.

Brownie et al.(1997) "The elimination of primer-dimer accumulation in PCR," *Nucleic Acids Research* 25(16):3235-3241.

Carmon et al.(2002) "Solid-Phase PCR in Microwells: Effects of Linker Length and Composition on Tethering, Hybridization, and Extension," *BioTechniques* 32(2):410-420.

Nazarenko et al.(2002) "Multiplex quantitative PCR using self-quenched primers labeled with a single fluorophore," *Nucleic Acids Research* 30(9):e37, 7 pages.

International Search Report and Written Opinion for International Application No. PCT/GB2008/002273, dated Nov. 26, 2008, 14 pages.

* cited by examiner

1. Hybridization and Forward Primer extension:

2. Detect "forward strand" with a probe:

3. Reverse Primer extension:

4. Detect "reverse strand" with a probe:

HIGH MULIPLEX NUCLEIC ACID AMPLIFICATION

This application is the U.S. national stage of international patent application PCT/GB2008/002273, filed Jul. 3, 2008, which claims the benefit of and priority to GB Patent Application No. 0712882.0, filed on Jul. 3, 2007.

This invention relates to the simultaneous amplification of multiple nucleic acid target sequences.

Known approaches to the simultaneous amplification of multiple nucleic acid target sequences, for example by multiplex PCR, can be split into solution-phase and surface-based procedures.

The simplest reported solution-phase methods attempt to optimise PCR conditions so that many different primer pairs can work together in a single tube without creating excessive primer-dimer artefacts or other undesirable amplicons which cause amplification to fail. This approach is limited, and in most cases even 10-plex reactions of this type fail. More sophisticated methods attempt to modify the target sequences to give them common primer domains at their ends, so that bulk amplifications can use a single pair of primers. One way to achieve this is to design target-specific primers such that they all carry one common amplification sequence at their 5'-end, and use these at low level and/or for only a few cycles prior to bulk-amplification with a common primer (Brownie, Shawcross et al. 1997). Use of a single common primer will further eliminate amplification of short primer-dimers, since they will form stable panhandle structures that are refractory to PCR priming.

Alternative solution-phase methods employ two different common sequences in the forward and the reverse primers. This has been done in a multi-step reaction, with all the forward primers containing a tail sequence (T1) in a first PCR, followed a nested second PCR that introduces the second tail sequence (T2). A third PCR can then be performed using only the two common sequences T1 and T2 as primers (Lin, Cui et al. 1996).

The number of reactions and the number of primers needed can be reduced if the DNA is first digested with one or more restriction enzymes, followed by its ligation to adaptor sequences. Multiplex PCR can then be performed with one specific primer for every target and one common primer based on the adaptor sequence (Broude, Zhang et al. 2001). This approach essentially halves the number of PCR primers used in comparison to the simplest form of multiplex PCR, but these many primers can and will still interact with each other to generate amplification artefacts. The specific primer can also be designed to carry a common tail sequence, so that after a number of initial cycles all the targets can be co-amplified with just one primer pair (Shapero, Zhang et al. 2004).

Another reported strategy is to reduce the target sequence complexity by first applying a pre-amplification step that entails long-range PCRs, followed by simple multiplex PCR using the long product mixture as the template (Li and Vijg 1996). This approach is obviously only valid if the targets are suitably clustered to be grouped into practical long-range amplifications.

A very different approach to solution-phase multiplex PCR uses 'Selector probes' (Dahl, Gullberg et al. 2005). These are double-stranded synthetic reagents that have common sequences internally and single-stranded extensions at their ends that are specifically matched to the intended targets abutting restriction sites. One selector probe is synthesized for each different target. Input DNA is digested by the appropriate restriction enzyme(s), mixed with the pool of selector probes, and allowed to hybridize to form circular molecules that involve one selector probe joined to one target restriction fragment. A ligase reaction then covalently closes these circles. Finally, after removing all non-circular species, a PCR with two primers that match the common selector probe sequences is used to mass-amplify the set of captured DNA fragments.

High-multiplex PCR using emulsion droplets has also been reported. In this technology, individual DNA fragments are separated from each other into tiny water droplets suspended in a water-oil emulsion. The DNA fragments are pre-processed to carry common tail sequences, and the water droplets harbour all the necessary reagents to execute PCR. The droplets therefore behave like separate reaction vessels, and prevent amplification products interfering with each other. This method is designed to amplify all the DNA fragments in the starting DNA not just a specific subset of sequences.

Known surface-based strategies for multiplex PCR physically separate the primer pairs (at different locations on a surface or on distinct particles); in order to limit the otherwise immense opportunities for primer-dimer artefact generation and for misprimed input DNA amplification. Procedures generally attempt to conduct the whole PCR process on the surface—but this is very inefficient and difficult to control.

In surface-based procedures, either one or both primers from each primer pair may be immobilized on the surface (via their 5'-ends). In either case, one or both primers from each primer pair may also be added to the solution-phase to increase the amplification efficiency (which is otherwise extremely low due to surface chemistry effects and surface-based reaction kinetics). This, however, goes against the main motivation for developing these methods in the first place: to overcome problems associated with having too many primers in solution.

Low-level amplification with both primers attached to a solid support has been reported in 'Bridge Amplification' (Bing, Boles et al. 1996), wherein the primers were attached to a range of different bead types. Results were presented based upon genomic DNA, but amplification efficiencies were very low and about ⅓ of the generated product (and at least as much of the surface primers) ended up not being bound to the beads but free in solution. A similar reaction was demonstrated for primers bound to glass slides (Adessi, Matton et al. 2000), but this used only previous PCR products as DNA template and not genomic DNA (presumably due to innate reaction inefficiencies). This study also showed that a maximum of around 60% of the surface primers remained attached to the surface at the end of the procedure. The excessive release of surface primers into solution observed in these two reports is a major drawback which leads to the same risk of artifact generation as occurs in simple solution-phase multiplex PCR.

Other surface-based multiplex PCR strategies have been reported in which the solid surface is replaced by polyacrylamide gel pads on arrays or by gel particles in solution. These gel structures hold the primers both on and inside them, and reacting molecules can diffuse to greater or lesser degrees through the gel matrix. Reactions in these matrices are much more akin to solution-phase experiments (in their diffusion, hybridisation, and kinetic properties) and this is why they are used. However, gel pads/particles are very difficult to prepare, store, and use in automated settings. Shapero et al (2001) demonstrated a 57-plex PCR from genomic DNA, amplifying products from 70 to 1300 base pairs, using acrylamide beads. When using gel pads (Tillib, Strizhkov et al. 2001) the input DNA is first hybridised to the bound primers and then this solution is replaced by mineral oil to prevent any reactant communication between reaction pads.

A gel pad method, 'multiplex microarray-enhanced PCR' (MME-PCR) (Pemov, Modi et al. 2005) has been described in which the bound primers are divided in two segments; 3'-end sequences that are target-specific, and 5'-end sequences that contain either of two common/universal sequences U1 and U2. The goal of MME-PCR is still to execute the whole amplification on/in the gel pads, but to improve the amplification efficiency common primers that are complementary to U1 and U2 are included in the PCR solution. This then continually produces extra template molecules in solution that can interact with the surface bound primers. The method has managed to achieve a multiplex amplification using six primer pairs from genomic DNA. However, the method is only demonstrated on bacterial DNA where the standard amount of DNA was large, and major primer-dimer artefacts were apparent in the results product.

The present inventors have developed a method of amplifying multiple nucleic acid target sequences which minimises the production of primer dimer artefacts and is therefore suitable for amplifying large numbers of target sequences simultaneously. In these methods, the production of primer dimer artefacts scales additively with the number of targets in the multiplex and so does not become dramatically exaggerated or overwhelm the amplification of target sequence upon high levels of target multiplexing.

An aspect of the invention provides a method of amplifying one or more target regions in a nucleic acid sample comprising;
(i) providing forward and reverse compound primers immobilised on the surface of a solid support,
   wherein said forward and reverse compound primers comprise a common amplification sequence and a specific primer sequence,
   the specific primer sequences of the immobilised forward and reverse compound primers being hybridisable to the one or more target regions of the nucleic acid sample,
(ii) hybridising a non-priming barrier oligonucleotide to the common sequences of the immobilised forward and reverse compound primers,
(iii) hybridising a template strand of the nucleic acid sample to the specific primer sequence of the forward compound primers,
(iv) extending the forward compound primers along the template strand to produce immobilised first extension products comprising the compound primer and the complementary sequence of the one or more target regions of the template strand of the nucleic acid sample,
(v) hybridising the first extension products to the immobilised reverse compound primers,
(vi) extending the reverse compound primers along the first extension products to produce immobilised second extension products comprising the sequence of the reverse compound primer, the template strand of the nucleic acid sample in the target region and the complement of the forward compound primer, and,
(vii) amplifying the immobilised second extension products using common primers which hybridise to the complement of the common sequences of the forward and reverse compound primers to produce amplified nucleic acid molecules in solution which comprise the one or more target regions.

Methods of the invention are particularly suitable for simultaneously amplifying more than one target region in the nucleic acid sample (i.e. multiplex amplification), for example at least 10, at least 50 or at least 100 target regions.

The forward and reverse compound primers are oligonucleotide molecules which comprise common amplification sequences and specific primer sequences suitable for amplification of a target region of the nucleic acid sample.

The common amplification sequence is a sequence of from 15 to 80 nucleotides, preferably 15 to 40 nucleotides, which is the complement of a target sequence for the hybridisation of a common primer or, optionally, two nested common primers.

The common amplification sequence may be the same or different in the forward and reverse primers of the compound primer pair. Where the common amplification sequences are the same in both the forward and reverse primers of the pair, the immobilised extension products may be amplified by common amplification primers which have the same sequence. Where the common primer sequences are different in the forward and reverse primers of the pair, the immobilised extension products) may be amplified by a pair of amplification primers having different sequences.

The common primer may comprise or consist of a nucleic acid sequence which is identical to the common amplification sequence or a nucleic acid sequence which has 80% or more, 90% or more or 95% or more sequence identity with the common amplification sequence and is capable of hybridising to the common amplification sequence under suitable hybridisation conditions, such that the common primer primes extension of a new strand along the template strand. The common primer may be at least 8, 10, 12, 16, or 20 bases long.

The common amplification sequence and the common primer may be of any convenient sequence and the skilled person is readily able to identify suitable sequences.

In some embodiments, the common amplification sequence may form a target for nested amplification by two pairs of common primers. For example, the common amplification sequence may comprise a 5' region for hybridisation with a member of a first pair of amplification primers and a 3' region for hybridisation with a member of a nested pair of amplification primers.

The specific primer sequence is a sequence of from 5 to 50 nucleotides, preferably 15 to 40 nucleotides, which is located 3' to the common amplification sequence in the compound primer sequence. The specific primer sequence may, for example, be at least 5, 6, 8, 10, 12, 16, or 20 bases long.

The specific primer sequence may comprise or consist of a nucleic acid sequence which hybridises to a first strand of the target region such that the sequence primes the polymerisation of a new strand comprising the target region, which is complementary to the first strand. The specific primer sequence may comprise or consist of a nucleic acid sequence which is identical to sequence in the target region, or nucleic acid sequence which has 80% or more, 90% or more or 95% or more sequence identity with the target region of the nucleic acid sample and is capable of hybridising to a strand of the nucleic acid sample of target region under suitable hybridisation conditions.

The specific primer sequences of the forward compound primers are hybridisable to a template strand of the nucleic acid sample so as to prime polymerisation across the one or more target regions to produce first extension products comprising said target regions.

The specific primer sequences of the reverse compound primers are hybridisable to the first extension products so as to prime polymerisation across the target regions of the first extension products to produce second extension products comprising said target regions.

In some embodiments, the specific primer sequences of each pair of compound primers may hybridise to more than one target region in the nucleic acid sample. In such embodiments, a short specific primer sequence, for example 5-8 nucleotides, may be preferred. In other embodiments, the specific primer sequences of each pair of compound primers may hybridise uniquely to a single target region in the nucleic acid sample. In such embodiments, a long specific primer sequence, for example, at least 16 nucleotides may be preferred.

The forward specific primer sequence of the pair of compound primers may be complementary to the nucleotide sequence at one end of a target region and the reverse specific primer sequence of the pair of compound primers may be complementary to the nucleotide sequence of the opposite strand at the other end of the target region, to allow amplification of the target region.

The skilled person is readily able to design suitable specific primer sequences for any desired target region using routine techniques in the art.

Primers and barrier oligonucleotides as described herein are oligonucleotides which bind to a target sequence through one or more types of chemical bonds, usually through complementary base pairing and usually through hydrogen bond formation. The primer may include natural (i.e. A, G, C, or T) or modified bases (7-deazaguanosine, inosine, etc.). In addition, the bases in a primer may be joined by a linkage other than a phosphodiester bond, so long as it does not interfere with hybridization or primer extension.

The pair of compound primers are immobilised onto the surface of a solid support. A solid support is an insoluble, non-gelatinous body which presents a surface on which the oligonucleotide primers can be immobilised. Preferably, the oligonucleotide primers form a monolayer on the surface of the support i.e. a single layer of oligonucleotide molecules attached to the surface of the support.

Solid-phase reactions using primers attached to the surface of a solid body as described herein do not include reactions using primers fixed within a matrix, such as gel.

Examples of suitable supports include glass slides, microwells, membranes, or microbeads. The support may be in particulate or solid form, including for example a plate, a test tube, bead, a ball, filter, fabric, polymer or a membrane. An oligonucleotide may, for example, be fixed to an inert polymer, a 96-well plate, other device, apparatus or material which is used in a clinical or investigative context. The immobilisation of oligonucleotide primers to the surface of solid supports is well-known in the art.

In some embodiments, the solid support itself may be immobilised. For example, microbeads may be immobilised on a second solid surface.

The compound primers are immobilised on the surface through their 5'-ends. This allows the priming of amplification reactions from the free 3' end of the compound primers.

Preferably, the compound primers are immobilised on the surface through a spacer which separates the primers from the surface. Examples of suitable primers include molecular polymers, such as alkyl chains, proteins or nucleic acids, for example polyT, polyA, polyG or polyC. If the spacer is a nucleic acid molecule, it is preferably linked to the compound primer by a carbon chain linker to reduce unwanted priming events.

In some embodiments, the compound primers may be biotinylated and attached to the surface via a biotin-streptavidin linkage with strepavidin forming the spacer.

The methods described herein are particularly suitable for the simultaneous amplification of high numbers of target regions in the nucleic acid sample (i.e. a high degree of multiplexing).

In preferred embodiments in which multiple target regions in the nucleic acid sample are amplified simultaneously, multiple pairs of compound primers may be immobilised on the solid support, each pair of compound primers comprising specific primer sequences for a particular target region of the sample.

Each pair of compound primers may be immobilised in a discrete zone on the surface of a solid support. The surface of the support may comprise multiple zones, each zone having a different compound primer pair immobilised thereto. For example, the surface may comprise at least 10, 50, 100, 1000, 10000, or 100000 different zones, each zone having a different compound primer pair immobilised thereto, such that the compound primer pairs in each zone on the surface amplify a different target region of said nucleic acid sample.

Each zone comprising a different compound primer pair may be located in a particular defined position on the support. Arrays of immobilised nucleic acid are well-known in the art and may be produced in a number of ways. For example, the compound primers synthesized ex situ using an oligonucleotide synthesis device, and subsequently deposited using a microarraying apparatus or synthesized in situ on the microarray using a method such as piezoelectric deposition of nucleotides.

In some embodiments, all the multiple pairs of compound primers on the support comprise the same common amplification sequence or the same pair of common sequences. This allows amplification of all the immobilised amplification products produced by all the compound primer pairs with a single common primer or a single pair of common primers.

In other embodiments, different subsets of the multiple pairs of compound primers on the support may comprise different common amplification sequences or pairs of common sequences. This allows the amplification of particular subsets of target regions using each pair of common primers. For example, the subset of target regions located on a particular chromosome may be specifically amplified using a single pair of common primers.

The barrier oligonucleotide hybridises to the immobilised compound primers to make them partially double stranded. This decreases the flexibility of the compound primers and reduces interaction between the compound primers which may otherwise lead to unwanted priming events.

Preferably, the barrier oligonucleotide hybridises to an immobilised compound primer before primer extension. For example, the barrier oligonucleotide may hybridise to the immobilised compound primer before, after or at the same time as the template strand or first extension product.

A suitable barrier oligonucleotide may comprise at least 5, 10, 15 or 20 nucleotides, and is preferably shorter than the compound primer to which it hybridises. For example, in some embodiments, the barrier oligonucleotide may be up to 30, 40, 50 or 60 nucleotides.

In some embodiments, the barrier oligonucleotide may hybridise to all or part of the common amplification sequence and, optionally, to one or more residues of the specific priming region of the compound primer, for example, up to 10 nucleotides. For example, the barrier oligonucleotide may comprise a nucleotide sequence which is complementary to all or part of the common amplification sequence and, optionally, one or more residues of specific priming sequence of the compound primers, or a nucleotide sequence which has 80% or more, 90% or more or 95% or more sequence identity with this sequence and is capable of hybridising to the compound primer under suitable hybridisation conditions.

In preferred embodiments, the barrier oligonucleotide hybridises to all or part of the common amplification sequence of the compound primer. For example, the barrier oligonucleotide may comprise a sequence which is complementary to all or part of the common amplification sequence of the compound primers or sequence which has 80% or more, 90% or more or 95% or more sequence identity with this sequence and is capable of hybridising to the compound primer under suitable hybridisation conditions.

The barrier oligonucleotide is non-priming and additional nucleotides cannot be added to its 3' end by nucleic acid polymerases. This prevents the barrier oligonucleotide from priming unwanted amplification reactions. Barrier oligonucleotides may be made non-priming by any convenient technique, for example, by the addition of a 3' phosphate group, using routine techniques.

The hybridisation of oligonucleotides and primers to target sequences in the present methods may be achieved using standard techniques. Specific hybridisation is routinely achieved in the art using high stringency conditions. Typically, high stringency conditions include a hybridisation temperature which is close to the predicted melting temperature of the primer or oligonucleotide in the hybridisation buffer.

Suitable hybridisation conditions for use in the present methods can readily be identified by the skilled person. Examples of suitable conditions and protocols are well-known in the art and are described, for example, in Molecular Cloning: a Laboratory Manual: 3rd edition, Sambrook & Russell (2001) Cold Spring Harbor Laboratory Press NY and Current Protocols in Molecular Biology, Ausubel et al. eds. John Wiley & Sons (1992).

The nucleic acid sample for use in the present methods may be obtained from any convenient source, for example from cultured cell lines, or primary cells, such as cells obtained from a healthy donor or from a patient having a medical condition, for example cancer cells. Any type or subset of cells may be used as a source of the nucleic acid sample. The nucleic acid sample may be a DNA sample, preferably, a complex DNA sample, for example, a genomic DNA from a eukaryote, for example a mammal such as a human. A suitable sample may, for example, consist of 10 μg, 1 μg, 100 ng or less of genomic DNA, typically of mammalian origin, for example, human. A DNA sample may be obtained using any convenient technique. In other embodiments, the nucleic acid may be a sample of cDNA or RNA.

Any target regions of interest in the nucleic acid sample may be amplified as described herein. For example, some or all of the exons in the nucleic acid sample may be amplified as described herein. The nucleotide sequence of any target region of interest is available from sequence databases and suitable primers may be designed and synthesised using routine techniques.

In some embodiments, the nucleic acid sample may be pre-amplified in solution to produce products which have an increased concentration of the one or more target regions relative to the original nucleic acid sample. This increases the efficiency of the subsequent amplification and reduces the required amount of nucleic acid sample required. The nucleic acid sample may be so enriched by amplifying the one or more target regions in a DNA sample in solution using specific amplification primers. The products of this amplification are enriched for the target regions. For example, 15-30 cycles of amplification may be performed on the nucleic acid sample using primers specific for the one or more target regions.

Techniques for the amplification of known target regions in a DNA sample using specific amplification primers are well-known in the art.

This pre-amplification increases the number of copies of the target regions over other sequences in the nucleic acid sample, so improving the yield and effectiveness of the subsequent amplification steps.

Before hybridisation and amplification, the nucleic acid sample or a pre-amplified product thereof may be made single-stranded to produce the template strand. This is conveniently achieved by heat denaturation. Suitable conditions for the denaturation of nucleic acids are well-known to those of skill in the art. For example, the template may be heated to 90° C. or greater, typically 95° C.

Following denaturation of the nucleic acid sample or pre-amplified product thereof to produce the template strand, the template strand and forward compound primer may be exposed to conditions which allow the specific primer sequence of the compound primer to hybridise to the template strand at the target region. Suitable conditions for the hybridisation of nucleic acids are well-known to those of skill in the art and will depend on the sequences of the primer and template strand.

The template strand which is hybridised to the immobilised forward compound primer forms a template for extension of the primer across the target region of the nucleic acid sample. The forward compound primer is extended along the template strand using a DNA polymerase in accordance with conventional techniques to produce a first extension product which comprises the forward compound primer sequence at its 5' end and sequence complementary to the template strand of the nucleic acid sample. This sequence is located downstream (i.e. 3') of the forward compound primer sequence and comprises the target region of the nucleic acid sample. The first extension product remains immobilised on the support via the forward compound primer.

After the first extension, the template strand of the nucleic acid sample is separated from the first complementary nucleic acid molecule and preferably removed. This may be conveniently achieved by any convenient technique, for example denaturation by heat or NaOH, followed by washing the support to remove material not immobilised thereto.

In some embodiments, the template strand of the DNA sample or the pre-amplification product thereof may be recovered for subsequent use.

Following the separation of the template strand, the immobilised first extension product is hybridised to the specific primer sequence of the reverse compound primer. The first extension product thus forms a bridge or loop which links the forward and reverse primers of the compound primer pair.

The non-priming barrier oligonucleotide is hybridised to the common sequences of the reverse compound primer before the extension of the reverse compound primer. The barrier oligonucleotide may hybridise before, simultaneously with or after hybridisation of the immobilised first extension product to the specific primer sequence of the reverse compound primer.

The first extension product which is hybridised to the reverse compound primer forms a template for a second cycle of extension. The reverse compound primer pair is extended along the template of the first extension product to produce a second extension product which comprises the reverse compound primer sequence at its 5' end, sequence complementary to the first extension product downstream (i.e. 3') of the reverse compound primer sequence and the complement of the forward compound primer at its 3' end. The sequence which is complementary to the forward compound primer subsequently forms a target for hybridisation to the common amplification primers during the amplification in solution. The second extension product remains immobilised on the support via the second compound primer.

The first and second extension products are complementary to each other.

Following step (vi), the immobilised extension products (i.e. the first and second extension products) may be separated or purified from other reaction components, for example by washing the support to remove material not immobilised thereto.

Following step (vi), the 3' ends of non-extended compound primers on the surface of the solid support may be blocked to prevent further priming. Conveniently, the 3' ends of non-extended compound primers on the surface may be blocked by incorporating a dideoxynucleotide, such as ddATP, at the 3'-end of all the DNA molecules immobilised on the surface.

The immobilised second extension product may be amplified by standard amplification techniques, such as PCR, in solution using common primers which hybridise to the common amplification sequences of the compound primers located at the termini of the second extension product.

In some embodiments, the common primers may comprise an affinity tag or label that allows the isolation and/or purification of the amplification products, following primer extension. The affinity tag may be any molecule that binds specifically to another molecule. Examples of suitable tags include specific nucleotide sequences which are capable of hybridising to a complementary capture sequence, which may for example be immobilised on an array. Suitable nucleotide sequences for use as tags are well known in the art. Other suitable tags include biotin, which specifically binds avidin and streptavidin with high affinity.

Suitable solution phase amplification techniques are well known in the art and include the polymerase chain reaction (PCR) (reviewed for instance in "PCR protocols; A Guide to Methods and Applications", Eds. Innis et al, 1990, Academic Press, New York, Mullis et al, Cold Spring Harbor Symp. Quant. Biol., 51:263, (1987), Ehrlich (ed), PCR technology, Stockton Press, NY, 1989, and Ehrlich et al, Science, 252: 1643-1650, (1991)).

Amplification of the second extension product by the common primers produces amplified nucleic acid molecules in solution which comprise the target region.

The reaction medium may further comprise artefacts such as primer dimers. Preferably, the level of primer-dimer in the reaction medium is less than 50%, less than 20%, less than 10%, less then 5% or less than 1% of the total amplified nucleic acid molecules.

In preferred embodiments, the level of primer-dimer is insufficient to produce a visible band on an ethidium bromide gel.

Following amplification of the second extension product, the amplified nucleic acid molecules may be isolated and/or purified using standard techniques. In some embodiments, the amplified nucleic acid molecules may be isolated and/or purified by means of the affinity tag. For example, a binding pair member which binds to the affinity tag may be immobilised, for example on an array, affinity column or magnetic bead, and contacted with amplification products comprising the affinity tag. Products bound to the immobilised binding pair member may be washed and subsequently eluted using standard techniques.

In some preferred embodiments, the amplified nucleic acid molecules may be isolated and/or purified by means of a nucleotide sequence tag. For example, a complementary nucleotide sequence which binds to the nucleotide sequence tag may be immobilised on an array and contacted with amplification products comprising the nucleotide sequence tag. Only those products comprising the nucleotide sequence tag will bind to the immobilised complementary nucleotide sequence. These bound products may be washed and subsequently eluted using standard techniques.

Following amplification of the extension products, and, optionally, isolation and/or purification, the amplified nucleic acid molecules may be investigated further.

The amplified nucleic acid molecules may be subjected to genotyping techniques to identify one or more bases within the amplified target regions. Suitable genotyping techniques include sequencing and hybridisation based techniques.

For example, one or more amplified nucleic acid molecules may be sequenced, for example to identify or determine the presence of polymorphism or mutation within the target region. In some embodiments, parallel sequencing methods may be used to sequence multiple amplification products. Suitable methods include the GS20 sequencing method developed by 454 Life Sciences™ (CT USA). A polymorphism or mutation may be identified by comparing the sequence obtained with the known sequence of the target region, for example as set out in sequence databases. Alternatively, it can be compared to the sequence of the corresponding nucleic acid from a control DNA e.g. from sample cells. Sequencing may be performed using any one of a range of standard techniques.

In some embodiments, amplified nucleic acid molecules may be contacted with an array of immobilised nucleic sequences, e.g. for example to identify or determine the presence of polymorphism or mutation within the target region. A suitable array may comprise a population of genomic or specific oligonucleotide sequences immobilised on a solid support.

Prior to hybridisation with the sequences of an array, the amplified nucleic acid molecules may be labelled. Labelling of amplification products may be achieved by standard methods. For example, products may be amplified (linearly or exponentially) from an amplification product using synthetically labelled oligonucleotides (e.g. containing Cy5- or Cy3-modified nucleotides or amino allyl modified nucleotides, which allow for chemical coupling of the dye molecules post amplification), or modified or labelled nucleotides during the amplification reaction. Suitable labels include fluorescent labels, such as cyanine 3 or cyanine 5. The labelled extension products may then be hybridised to an array using standard techniques.

The nucleic acid sequences on the array to which the product hybridises may be determined, for example by measuring and recording the label intensity at each position in the array, for example, using an automated DNA microarray reader.

The presence or absence of hybridisation of an amplified nucleic acid molecules to a sequence displayed on the array may be indicative of the presence of polymorphism or mutation within the one or more target regions of the nucleic acid sample.

In other embodiments, the population of amplified nucleic acid molecules may be analysed in bulk. For example, the size range or distribution of the population may be determined.

Oligonucleotides and other reagents as described herein may form part of a kit for amplifying one or more target regions of a nucleic acid sample simultaneously, as described herein, preferably more than one target region (i.e. multiplex amplification), for example at least 10, at least 50 or at least 100 target regions e.g. in a suitable container such as a vial in which the contents are protected from the external environment.

A kit for use in amplifying one or more target regions of a nucleic acid sample as described herein may comprise;
(i) a solid support, and
(ii) one or more pairs of forward and reverse compound primers immobilised or immobilisable on the surface of the solid support,
   wherein said forward and reverse compound primers comprise a common amplification sequence and a specific primer sequence,
   the specific primer sequences of the immobilised forward and reverse compound primers being hybridisable to the one or more target regions of the nucleic acid sample, The kit may also include instructions for use e.g. in a method amplifying one or more target regions of a DNA sample simultaneously as described herein.

A kit may further comprise one or more non-priming barrier oligonucleotides for hybridising to all or part of the common amplification sequence of the compound primers.

A kit may further comprise common primers for hybridising to the complement of the common amplification sequence of the compound primers and producing amplification products in solution which comprise the one or more target regions.

The common primers may be labelled with a detectable label, for example a fluorescent label, or a tag which binds a detectable label. Suitable tags include biotin. If the common primers are labelled with a tag, the detection reagents may further comprise a detectable label that binds to the tag.

A kit may further comprise amplification reagents. Amplification reagents may include buffers, nucleotides, and thermostable DNA polymerase, as are well known in the art.

A kit may further comprise amplification primers specific for the one or more target regions for pre-amplifying the nucleic acid sample for the one or more target regions, prior to denaturation and hybridisation with the forward compound primer.

The kit may also comprise one or both of: apparatus for handling and/or storing nucleic acid samples obtained from the individual; and, reagents for extracting or purifying said nucleic sample from a sample of cells obtained from the individual, for example chaotropic agents such as GdHCl with or without detergent.

Various further aspects and embodiments of the present invention will be apparent to those skilled in the art in view of the present disclosure. All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described below.

FIG. 1 shows a schematic drawing of the immobilised compound primers.

FIG. 2 shows a schematic drawing of the MegaPlex PCR process. In step 1, distinct primer pairs are attached to separate locations on a solid support. The reaction at one location is illustrated. In step 2, target regions of single-stranded template DNA are primed and copied by the primers on the surface. In step 3, after removal of the template DNA, the other primer at each site hybridises to the first extension product and copies it to make it double-stranded. This product strand has acquired the common amplification sequence extensions at each end. In step 4, the second extension products are then bulk-amplified in solution by regular PCR employing a primer or primer pair that hybridises to the common amplification sequence extensions.

A) Lane 1: 50 bp DNA ladder. Lanes 2-6: 3-plex amplification reactions of targets of the same length; 100, 200, 300, 400 and 500 bp respectively. B) Lane 1: 50 bp DNA ladder. Lanes 2-4: 5-plex amplification of targets covering targets of different length: 100+200+300+400+500 bp in each multiplex. Lane 5: 15-plex reaction (a combination of the three 5-plex targets shown in Lanes 2-4. The lowest band of ~50 bp that is apparent in a number of these tracks represents primer-dimer artefacts generated between pairs of primers sitting on individual beads.

Figure 5:
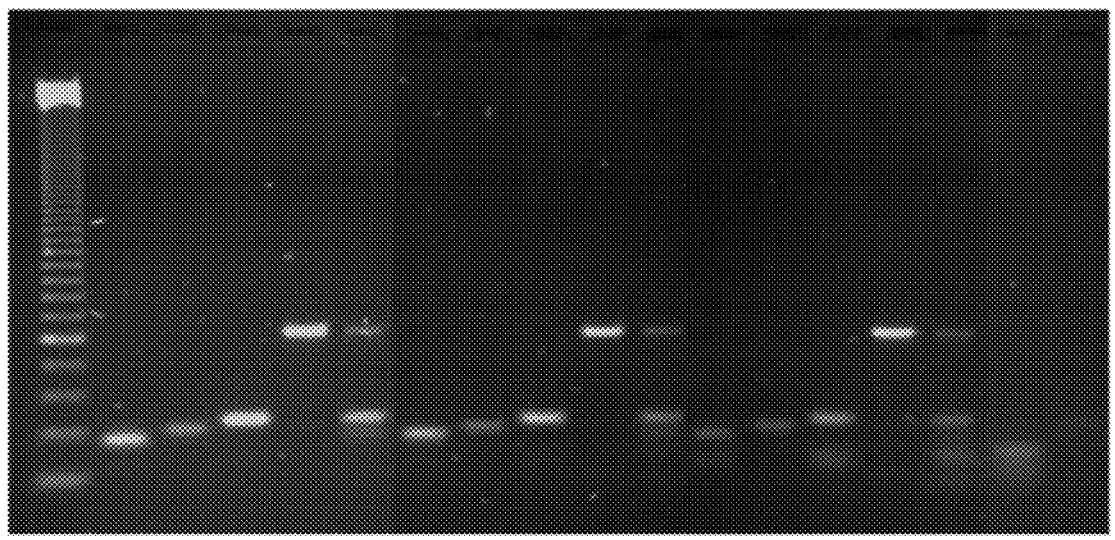

FIG. 5 shows the influence of genomic DNA concentration. Reaction products in lane 1-5 contained 5 μg human genomic DNA, lanes 6-10 contained 1 μg, and lanes 11-15 contained 200 ng. Lanes 16 and 17 were control reactions without DNA, and for lane 17 Taq Polymerase was also omitted for the surface extension reactions. Reactions in lanes 1, 6 and 11 were designed to generate a 94 bp product; lanes 2, 7 and 12 a 105 bp product; lanes 3, 8 and 13 a 115 bp product; lanes 4, 9 and 13 a 266 bp product; and lanes 5, 10 and 15 a 4-plex product (the combined targets from the first four reactions).

Figure 6:
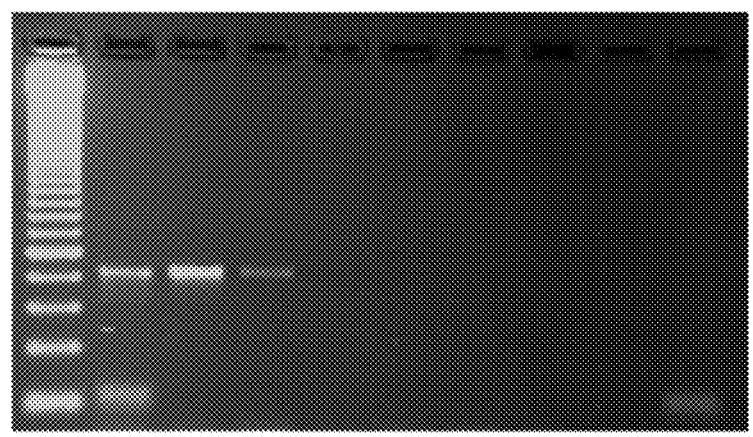

FIG. 6 shows the effect of surface-bound primer concentration. Single-plex amplification of human genomic DNA was conducted for a ~200 bp target. Lane 1: 50 bp DNA ladder. Products from the reaction with the highest surface primer concentration, in which the support surface was coated using a 1 μM primer solution, were run in lane 2, and decreasing concentrations of primer generated results shown in lanes 3-9 (using solutions of primer at concentrations of $10^{-2}$, $10^{-2}$, $10^{-5}$, $10^{-2}$, $10^{-9}$, $10^{-11}$, and 0 μM, respectively). The lane 10 reaction that also employed the primer solution with the highest primer concentration (1 μM) but without any template DNA, can be seen to generate only primer-dimers.

Figure 7:
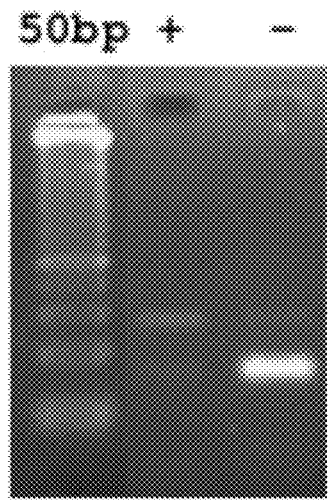

FIG. 7 shows reactions with (+) and without (−) the use of Barrier Oligos. The desired product should be 140 base pairs, but without the use of 'barrier oligos' the primer-dimer of ~70 base pairs is preferentially recovered.

Figure 8:
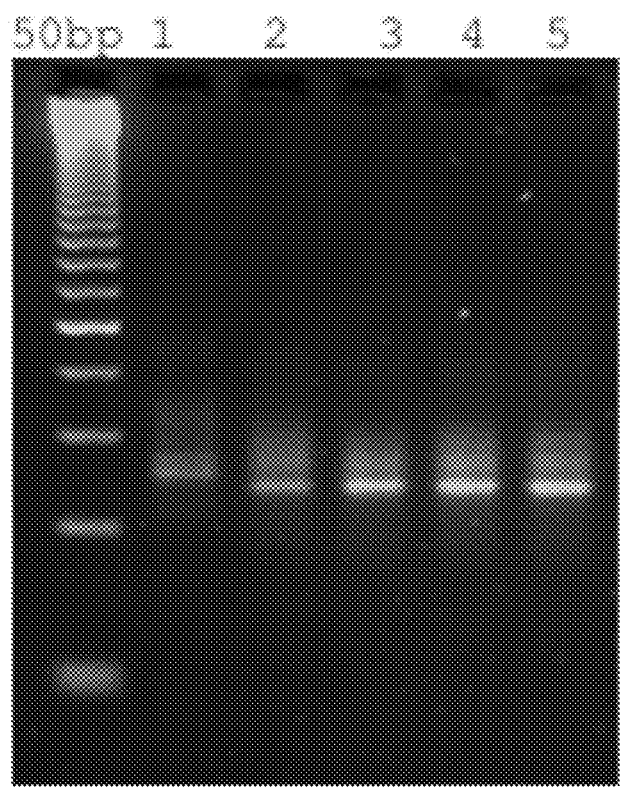

FIG. 8 shows MegaPlex PCR products from reactions employing pre-amplified template DNA. Lane 1; products from a 10-plex pre-amplification using 0.1 μM of each target-specific primer. Lane 2; products from a 25-plex pre-amplification using 0.1 μM of each target-specific primer. Lanes 3-5; products from 50-plex pre-amplifications using 0.1, 0.03 and 0.01 μM of each primer respectively.

Figure 9:
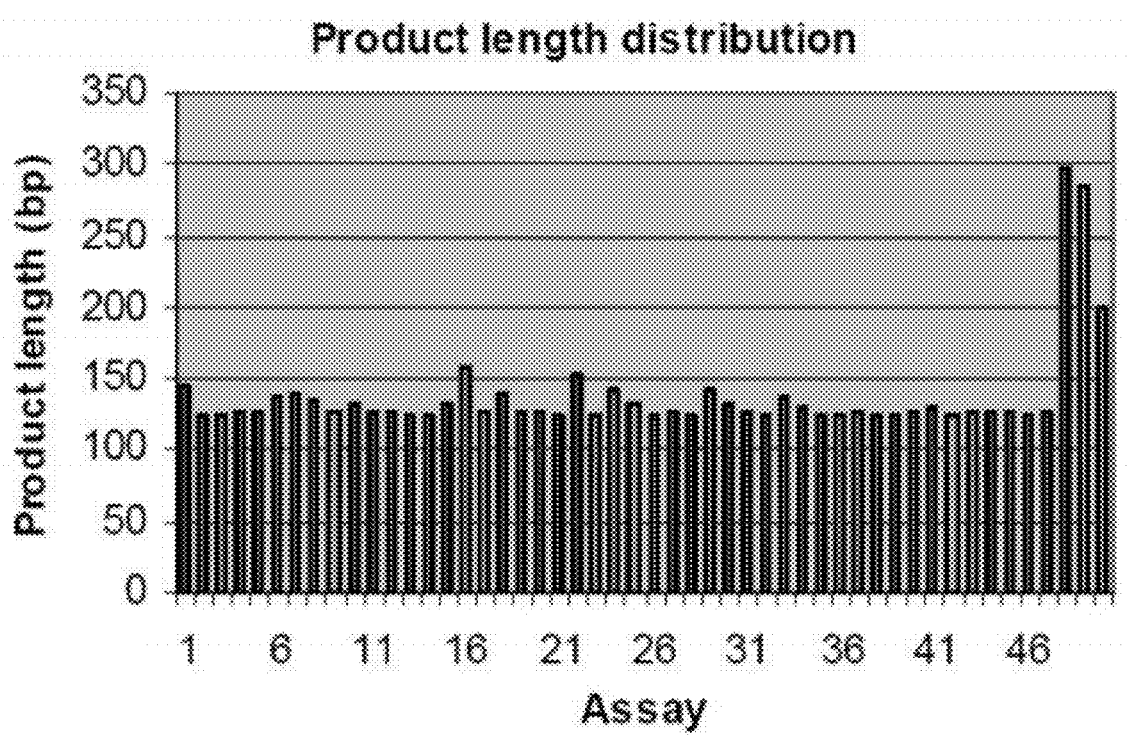

FIG. 9 shows the expected product length distribution for the 50-plex PCR reaction.

EXAMPLES

Materials and Methods

Oligonucleotides

All oligonucleotides were obtained from Biomers.net GmbH, Germany. Sequences are shown in Table 1.

Binding Primers to Solid Supports

To test and validate the MegaPlex-PCR principles, a number of pilot experiments were performed. Various primer pairs were equipped with biotin at their 5' end, enabling them to be attached by streptavidin-biotin interaction to either streptavidin-coated polypropylene membranes (GHP Membrane 0.2 µm from Pall, coated with streptavidin by BioTeZ GmbH, Germany) or to streptavidin-coated magnetic beads (Dynabeads MyOne streptavidin C1, Dynal Biotech/Invitrogen). The membranes provide a solid reaction surface, whereas the beads can be processed as a freely dispersed mixture in solution or after immobilisation onto some other solid surface (e.g., the walls of wells in a microtiter plate). This latter option is particularly suitable for an automated version of MegaPlex PCR.

For membrane experiments, the pairs of primers were transferred from a 384-well microtiter plate to distinct locations on a membrane (via a centrifugation procedure). The primers were diluted as a pair in HEN buffer (0.1 M Hepes, 10 mM EDTA, 50 mM NaCl, pH 7.5) to a concentration of 0.02-0.5 µM and typically 5 µL of this mixture was applied to each membrane feature (0.1-2.5 pmol per primer). After allowing to bind for 30 minutes at room temperature the membranes were washed in 0.1M NaOH followed by a rinse in HEN buffer. Alternatively, for smaller scale tests, a small piece of membrane was soaked in primer solution for 30 min, and then washed in 0.1M NaOH and HEN buffer.

For bead experiments, pairs of 5'-biotinylated primers were bound to Dynabeads following the manufacturer's protocol. Aliquots of 5 µL of beads per target were washed twice in 2× Binding and Washing (B&W) buffer (10 mM Tris-HCl (pH7.5), 1 mM EDTA, 2.0 mM NaCl) and resuspended in double the initial volume. For each wash the beads were separated from the solution using a magnetic stand. The beads were then mixed with an equal volume of an appropriate pair of biotinylated primers diluted in water (typically 0.02-0.5 µM), and binding was allowed to proceed by incubating at room temperature for at least 15 minutes whilst gently agitating. The beads were then washed twice in 1×B&W buffer and finally resuspended in PCR buffer. Mixtures of beads carrying primer pairs were then made according to the needs of the planned MegaPlex PCR experiment.

In studies where beads were to be immobilised on the walls of a microtiter plate, a streptavidin coated plate (ChoiceCoat Streptavidin plate from Pierce) was first treated with biotin-BSA (Sigma) to block non-specific DNA/protein binding sites on the plastic. The biotin-BSA was diluted to 40 µg/ml in 1×B&W buffer and 40 µl was added to each well of the plate. This was left to incubate at room temperature for 2 hours. The wells were the washed with 1×B&W buffer, and 30 µl of primer-carrying beads in 1×B&W buffer was transferred to each well and left to bind to the wells at room temperature for at least one hour. The wells were then washed in PCR buffer twice, before proceeding with the MegaPlex PCR procedure.

Megaplex Amplification from Genomic DNA

Figure 2:
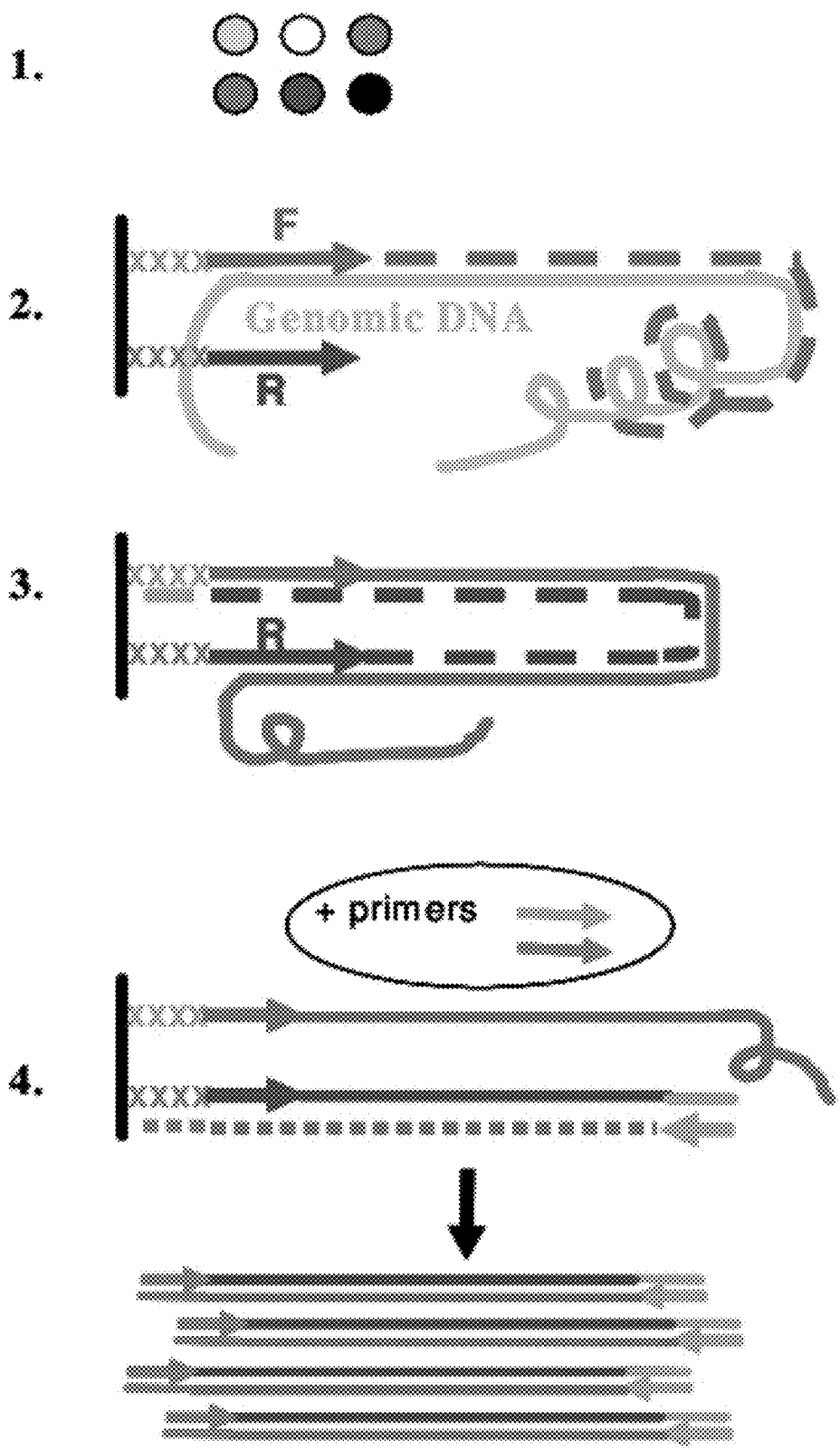

The Megaplex amplification method is shown schematically in FIG. 2.

a) Solid-Phase Primer Extension

Membranes or beads were loaded with appropriate primer pairs and washed in PCR buffer, as described above. Complex genomic DNA for use as template was denatured by placing in a boiling water bath for minutes, followed by direct cooling on wet ice. This template DNA (typically 0.1-2 µg for human genomic DNA) was allowed to hybridise to the membrane/beads with their surface-bound primers via an overnight incubation at 45° C. in PCR tubes containing PCR buffer without Taq polymerase or nucleotides (1× Amplitaq Buffer, 1.5 mM MgCl2, 5% Dimethylsulphoxide (DMSO)).

To initiate the first extension cycle, additional PCR buffer was added to bring the final concentration of dNTPs to 0.2 mM and to add 0.04 U/µl AmpliTaq Gold (Applied Biosystems). The extra reaction mix was pre-activated at 94° C. for 10 minutes (to activate the AmpliTaq Gold enzyme), and it was then cooled to annealing temperature before being added to the annealing reaction. Primer extension is allowed to proceed for 5 minutes at 45-55° C. followed by 5 minutes at 65° C. The reaction was stopped by adding 20-30 µl of 0.5M EDTA, and the solid support was washed in 0.1M NaOH to remove (recover) the template DNA, followed by rinsing in PCR buffer. The recovered input DNA was not damaged by the MegaPlex procedure and so it could, in principle, be reused in additional MegaPlex or other experiments. For the second extension cycle, the same procedure was repeated. This was started by incubating the bead/membrane support for 5 minutes at 45-55° C. to let the first extension products bind to the other primer in each pair (with no genomic DNA now present), followed by the extension, stopping, and clean-up steps.

b) Blocking of Non-Extended Primers

Non-extended surface-bound primers are preferably deactivated at their 3'-ends after the second extension step (i.e., made unable to prime polymerisation reactions). This prevents them from giving rise to any undesirable amplification products during the subsequent PCR cycles should they break free of the surface and move into solution (this will happen for a fraction of them since biotin-streptavidin interactions are not very stable to heat). This was achieved by incorporating ddATP at the 3'-end of all DNA molecules on a MegaPlex surface. The reaction for this contained 0.05 U/ul TdT (Terminal deoxynucleotide Transferase, Amersham Biosciences/GE Health Care) and 0.5 mM ddATP in 1× TdTbuffer (Amersham Biosciences/GE Health Care), and it was incubated at 37° C. for 1 hour.

c) PCR with Common Primers

A standard solution-based PCR was conducted to bulk-amplify all the MegaPlex PCR products, using a single primer pair matched to the common tails of the surface bound molecules. Small sections of membrane or the beads from the experiment were placed directly into this PCR vessel. Alternatively, if the beads were bound to a microtiter plate well, this well was used as the PCR vessel. This PCR was typically of 20-30 µL volume and it contained 0.4 µM of each of the two common primers, 0.03 U/µL AmpliTaq Gold® polymerase (Applied Biosystems), 1× AmpliTaq Gold® Buffer, 2.5 mM $MgCl_2$, 5% DMSO, and 200 µM of each dATP, dCTP and dGTP, 100 µM dTTP and 300 µM dUTP and 0.02 U/ul of Uracil DNA glycosylase (Amersham Biosciences/GE Health Care). Thermal cycling consisted of an initial 10 minute activation step at 94° C., followed by 30 cycles of 94° C. for 15 seconds, 58° C. for 30 seconds, and 72° C. for 1 minute.

d) Pre-Amplification of Template DNA

In some situations a crude pre-amplification of desired targets in the input genomic DNA was undertaken before adding this reagent into the MegaPlex PCR procedure. This entailed a standard solution-phase high-multiplex PCR using, in a single mixture, primer pairs for all the target sequences. These primer pairs were designed to amplify at least the full stretch of each target fragment to be captured in the MegaPlex PCR experiment. For the pre-amplification, 50 ng human genomic DNA is included in a 20 µl reaction that contains 4 mM $MgCl_2$, 200 uM dNTPs, 2 U Amplitaq Gold, and 0.01-0.1 µM of each primer. Thermal cycling consisted of an initial activation step of 94° C. for 10 minutes, followed by 27 cycles of 94° C. for 15 seconds and 52° C. for 30 seconds.
Results
1. Demonstration of Specific Primer Extension on a Solid Phase The basic reaction conditions for solid phase PCR were established for membrane-bound primers by using a single-stranded DNA template and detecting the immobilized extension products by hybridisation with target-specific fluorescent oligonucleotide probes.

Figure 1:
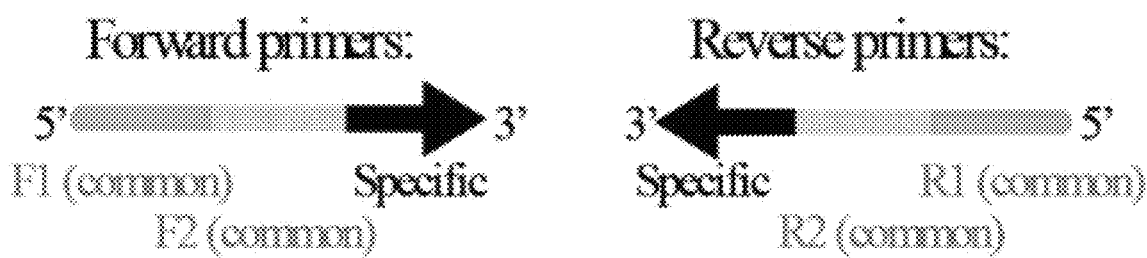
Figure 3:
FIG. 3 shows a demonstration of solid-phase primer extension. The reaction steps are shown schematically on the left, with pictures showing fluorescent signals on the array after the first and second primer extensions.
Figure 3:
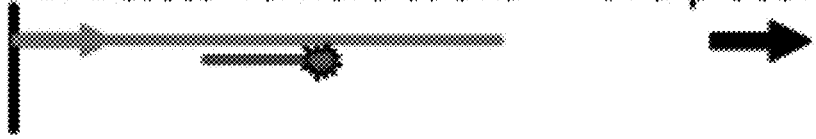
Figure 3:
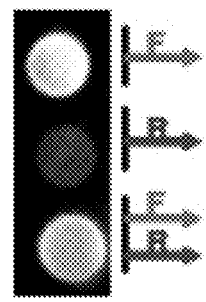
Figure 3:
Figure 3:
Figure 3:
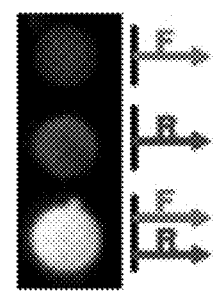

Forward (F: dT9U_X727U_B15b06F) and reverse (R: dT10_X727_B15b07R) primers for a specific sequence were attached to the same spot and to separate spots on a membrane array. A schematic of the primers is shown in FIG. 1. A single-stranded 50 base pair template (JB15-47P), complementary to the forward primer, was hybridized to the array (100 μl of a 2 μM solution). Primer extension was then achieved by placing the membrane in 100 ul PCR mix including 1× AmplitaqBuffer, 1.5 mM $MgCl_2$, 5% DMSO, 0.2 mM dNTPs and 0.03 U/μl AmpliTaq Gold (Applied Biosystems). The template DNA was then removed and the extension products were detected with a fluorescent oligonucleotide probe complementary to the extension product (HB15+31P). As shown in FIG. 3, fluorescence from the probe complementary to the extension product was detected only from features containing the forward primer. Features that contained only the non-specific reverse primer produced only low background fluorescence at the same level as no-probe or non-specific probe controls, showing that the extension product was specific and was only created from the forward target-specific primer.

To demonstrate extension of the reverse primer, the above membrane was alkali rinsed to remove the first fluorescent probe, and a second round of annealing and extension were conducted. At features that were set up to carry both the forward and the reverse primers, and only at those features, the reverse primer should now be able to bind to the first extension product and become extended along it. Before this newly synthesized strand can be tested for by hybridization, the first synthesized strand was removed from the array surface in order to prevent competition with the detection probes. This was achieved by including a deoxyuridine (dU) base in the first/forward surface-bound primer, so providing a residue that can be cleaved by Uracil DNA glycosylase. After conducting this cleavage and removing the first synthesized strand by an alkali rinse, a fluorescent probe (LB15R+01P) for the second synthesized strand was hybridised to the membrane. As illustrated in FIG. 3, only the spot that carried both the forward and the reverse primers produced a fluorescence signal, indicating that a specific reverse extension reaction had taken place.

2. Demonstrating Megaplex PCR with Human Genomic DNA as Template

Figure 4:
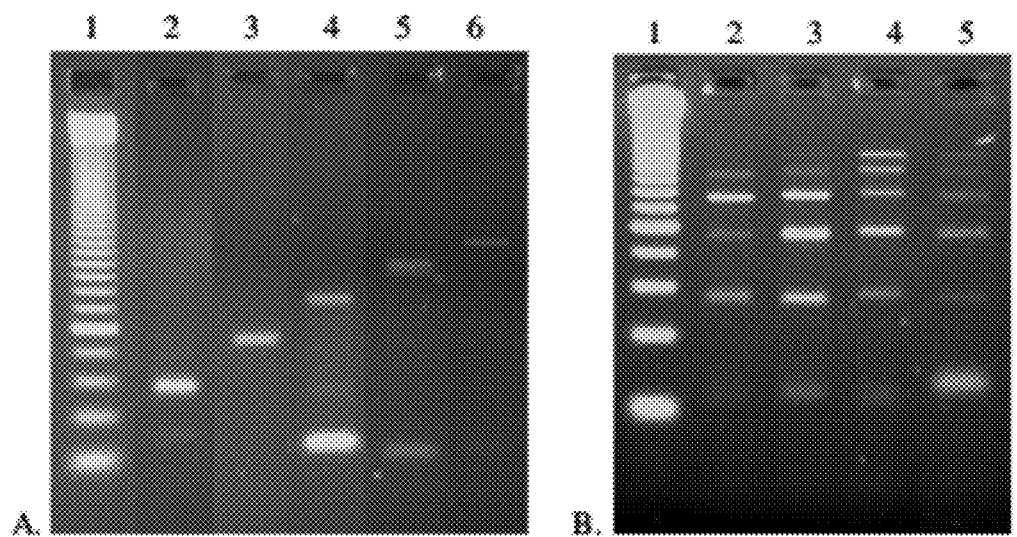
FIG. 4 shows amplification of human genomic DNA without pre-amplification or barrier oligonucleotides.

To demonstrate MegaPlex amplification from human genomic DNA, surface bound primers were designed for 15 independent sequences located on different chromosomes. This experiment used beads. Pairs of primers were designed to capture three different products each of ~100, ~200, ~300, ~400 and ~500 base pairs, and this set of designs also allowed us to study the effect of product length on the method. Five different MegaPlex reactions with targets of the same length, as well as three different combinations of 5-plex reactions for different sized targets were conducted. Additionally, all 15 primer pairs were combined in a single 15-plex reaction. Final products of all tested lengths were successfully detected by agarose gel electrophoresis (FIG. 4). Two of the 5-plex assays produced all five distinct products, clearly visible and separated on an agarose gel. The third 5-plex assay lacked only the largest product, though this may have actually been recovered but just at too low a level to detect by this gel analysis. The 15-plex reaction showed bands of all target sizes of fairly equal intensities. MegaPlex PCR with standard run conditions thus worked well on the first set of 15 random human genomic targets attempted, recovering molecules over a 5-fold size range.

In addition to the desired products, this experiment generated some short artefacts of the sort often seen in regular PCR and which typically overwhelm straightforward multiplex PCR assays. These artefacts are primer-dimers generated by low-level inter-primer annealing and extension within MegaPlex PCR features (i.e., not from such reactions between different primer pairs). More precisely these primer-dimers must be generated by cross-priming between the two different primers in a pair, rather than between two copies of any one primer in a pair. This is because, due to the formation of very short panhandle structures, the latter arrangement would be totally refractory to PCR amplification. The primer-dimer artefacts can be seen to vary in intensity between different multiplex combinations, but on average they represent only ~10% of the total amplified material.

Since these molecules are generated from within features (rather than between features) their production will scale additively with the number of targets in the multiplex. This is equally true for the desired target amplicons. Therefore, primer-dimer species will not become dramatically exaggerated or overwhelm the MegaPlex procedure upon higher levels of target multiplexing.

Primer-dimers represent the main obstacle in known multiplex PCR methods, and even for protocols similar in nature to the present methods, primer-dimers are shown in the published data to be a major amplification product that limits viability. The fact that they all but eliminated in the present methods herein constitutes a major advantage.

3. Optimal Genomic Template DNA Concentration

The effects of DNA concentration observed in three single-plex reactions and one four-plex reaction, comparing the outcome using 5 μg, 1 μg and 200 ng of human genomic DNA as template are shown in FIG. 5. This experiment was performed on beads. The amount of input DNA is seen to have a small but noticeable positive influence upon the amount of product generated. Additionally, the fractional amount of primer-dimer artefact produced increases as the amount of input DNA is decreased. Primer-dimers are most apparent in the no-DNA control (FIG. 5, lane 16).

MegaPlex amplification from around 100 ng of primary human genomic DNA has been found to be very successful, but no absolute lower limit has yet been established.

4. Effect of Surface-Bound Primer Concentration

High primer concentrations on the solid support were found to increase the degree of primer-dimer formation, independent of the amount of template DNA used. The following example, executed upon membrane arrays, showed how the relative levels of desired product and primer-dimer artefact are affected by dilution of the surface-bound primer (primers MPX:dT60×596-X727_LSCAN:b01A and MPX: dT60_Y596-Y727_LSCAN:b04B). As shown in FIG. 6, at the highest primer concentration in the study, the ~200 bp desired product was amplified in conjunction with a ~60 bp primer-dimer. By contrast, in reactions that used a lower amount of surface primers the 60 bp artefact disappeared leaving only the desired product. At even lower primer levels, the desired product also disappeared, indicating that the reaction has become too inefficient for target production. Recovery of primer-dimers in the last track, for which no template DNA was included in the reaction but the primers were present at the highest concentration, proved that primer-dimers are derived from primer sequences alone. Overall, this study demonstrates that the amount of surface-bound primers (and by extrapolation, their inter-molecular spacing) directly affected the level of primer-dimer production. The mechanism for this probably involves inter-primer annealing and extension, which becomes hindered when the primers are spaced too far apart to readily interact.

5. 'Barrier' Oligos

The ease with which surface-bound primers can interact was reduced by making these molecules double-stranded along a portion of their length. This reduced their flexibility and moved their 3'-ends further away from the surface, all of which made them less able to interact freely with adjacent surface primers. This modification may also have enhanced the ability of the primers to interact with genomic DNA since this is mostly located away from the reaction surface. The double-stranded primer regions were formed by synthesizing 'Barrier Oligos' that were complementary to the common tail sequences, and pre-annealing these in excess to the surface-bound primers. To prevent 3'-extension of Barrier Oligos at any stage of the procedure, they were modified upon synthesis to carry a 3'-end phosphate group. Longer Barrier Oligos that extend into the target specific sequences may be used, but in practice we found that this brought little extra benefit whilst adding significantly to the experiment cost and complexity (since different Barrier Oligos have to be synthesized for each MegaPlex PCR target).

The following example experiment was run on beads and employed 'Barrier Oligos' (MPX:X2:comp01A and MPX:Y2:comp01B). The experiment targeted a single DNA fragment using surface-bound primers MPX:T10:X2:rs12819884:b01A and MPX:T10:Y2:rs12819884:b01B, and it was run with and without Barrier Oligos. When Barrier Oligos were employed, 0.3 µM of each of the two oligonucleotides were included in the annealing solution (PCR buffer without Taq polymerase or nucleotides), both in the first extension cycle (with DNA present) and in the second extension cycle. As shown in FIG. 7, the amount of the longer target amplicon was increased, and the amount of the shorter primer-dimer artefact was dramatically decreased, when barrier oligos are present in the MegaPlex PCR.

6. Pre-Amplification of the Template DNA

Pre-amplification of the input DNA may be used to increase the efficiency of MegaPlex reactions and reduce the required amount of starting DNA template (especially important for precious genomic samples). The pre-amplification step entailed a standard solution-phase high-multiplex PCR applied directly to the test DNA before hybridizing this to the MegaPlex surface. This pre-amplification enriches the target sequences to a useful degree over most other sequences in the genome, so improving the yield and effectiveness of the subsequent MegaPlex PCR steps. The following example experiment, which was run on beads, utilised subsets of a set of 50 distinct targets processed as one 10-plex pre-amplification (0.1 µM of each primer), one 25-plex pre-amplification (0.1 µM of each primer), and three 50-plex pre-amplifications (0.1, 0.03 and 0.01 µM of each primer). Each of these pre-amplification products was then used as an input template for identical MegaPlex reactions that targeted the full set of 50 sequences used in the 50-plex pre-amplification. As shown in FIG. 8, the 10-plex pre-amplification generated only the expected products between 132-150 bp, whereas the 25-plex and the 50-plex pre-amplifications produced the full range of amplicon sizes from 125 bp to over 200 bp. The final product amplicons thus reflected the fragment subsets that were pre-amplified, and the overall reaction was very efficient as judged from the absence of primer-dimers.

TABLE 1

| Oligo Name | Chemistry | Oligo Sequence |
| --- | --- | --- |
| dT9U_X727U_B15b06F | 5'Biotin | TTTTTTTTIGAGCGAATTCTAGACTGCAGGCTGCATTTTGGCACAACCC (SEQ ID NO: 1) |
| dT10_X727_B15b07R | 5'Biotin | dT(10)_GAGCGAATTCTAGACTGCAGGGTTTCATTCCTGTTTGTCAGT (SEQ ID NO: 2) |
| JB15 - 47P | | GTTTCATTCCTGTTTGTCAGTTGTACGGTGGGTTGTGCCAAAATGCAGTT (SEQ ID NO: 3) |
| HB15 + 31P | 5'ROX | CAGTTGTACGGTGGGTT (SEQ ID NO: 4) |
| LB15R + 01P | 5'ROX | AACCCACCGTACAACTG (SEQ ID NO: 5) |
| Common primers: | | |
| MPX:X727: - 01A | | GAGCGAATTCTAGACTGCAGG (SEQ ID NO: 6) |
| MPX:Y727: - 02B | | GTCCGAATTCTAGACTGCCAC (SEQ ID NO: 7) |
| MPX:X596: - 01A | | TAGACGGGTCGACACGCGAGC (SEQ ID NO: 8) |
| MPX:Y596: - 02B | | TACGTTCCGGTAGCACGGTCC (SEQ ID NO: 9) |
| MPX:X13 - 01A | | GTTGTAAAACGACGGCCAGT (SEQ ID NO: 10) |
| MPX:Y13 - 01B | | CACAGGAAACAGCTATGACC (SEQ ID NO: 11) |

TABLE 1-continued

| Oligo Name | Chemistry | Oligo Sequence |
|---|---|---|
| Assay for primer concentration: | | |
| MPX:dT60_X596-X727_LSCAN:b01A | 5'Biotin + Spacer18 | dT(60)_18_TAGACGGGTCGACACGCGAGCGAATTCTAGACTGCAGGTAACTTACTAGG AGCTTTTAATGG (SEQ ID NO: 12) |
| mpx:dT60_Y596-Y727_LSCAN:b04B | 5'Biotin + Spacer18 | dT(60)_18_TACGTTCCGGTAGCACGGTCCGAATTCTAGACTGCCACAATAGAGTGAAA TGTATGATTGG (SEQ ID NO: 13) |
| 15 assays, 100-500 base pairs: | | |
| rs1544396:dT50_X596_X727_b10A | 5'Biotin + Spacer18 | dT(50)_18_TAGACGGGTCGACACGCGAGCGAATTCTAGACTGCAGGAGACTGGCGGGT AGAAAGG (SEQ ID NO: 14) |
| rs1544396:dT50_Y596_X727_b01A | 5'Biotin + Spacer18 | dT(50)_18_TACGTTCCGGTAGCACGGTCCGAATTCTAGACTGCCACTTCCTTCGCACT CTTAGGAT (SEQ ID NO: 15) |
| rs2614166:dT50_X596_X727_b10A | 5'Biotin + Spacer18 | dT(50)_18_TAGACGGGTCGACACGCGAGCGAATTCTAGACTGCAGGCATGGTAGTTTA GCTGGTTGAC (SEQ ID NO: 16) |
| rs2614166:dT50_Y596_Y727_bo2B | 5'Biotin + Spacer18 | dT(50)_18_TACGTTCCGGTAGCACGGTCCGAATTCTAGACTGCCACGCTCTATTTAAA GATGGCAAGA (SEQ ID NO: 17) |
| rs627839:dT50_X596_X727_b01A | 5'Biotin + Spacer18 | dT(50)_18_TAGACGGGTCGACACGCGAGCGAATTCTAGACTGCAGGTTCCCAGGGTCT CCTCCA (SEQ ID NO: 18) |
| rs627839:dT50_Y596_Y727_b02B | 5'Biotin + Spacer18 | dT(50)_18_TACGTTCCGGTAGCACGGTCCGAATTCTAGACTGCCACGGCAGCTCTTCC GTTCTCT (SEQ ID NO: 19) |
| rs3846382:dT50_X596_X727_b01A | 5'Biotin + Spacer18 | dT(50)_18_TAGACGGGTCGACACGGCGAGCGAATTCTAGACTGCAGGTTTATCAATTC CTGCTCAAACA (SEQ ID NO: 20) |
| rs3846382:dT50_Y596_Y727_b02B | 5'Biotin + Spacer18 | dT(50)_18_TACGTTCCGGTAGCACGGTCCGAATTCTAGACTGCCACCAAATCAGCAAT GATGGGATA (SEQ ID NO: 21) |
| rs2073454:dT50_X596_Y727_b10A | 5'Biotin + Spacer18 | dT(50)_18_TAGACGGGTCGACACGCGAGCGAATTCTAGACTGCAGGAGAGCTGGCCTG ATTCACTT (SEQ ID NO: 22) |
| rs2073454:dT50_Y596_Y727_b02B | 5'Biotin + Spacer18 | dT(50)_18_TACGTTCCGGTAGCACGGTCCGAATTCTAGACTGCCACACACTCACAAGA CCGATTTCC (SEQ ID NO: 23) |
| rs1041823:dT50_X596_X727_b01A | 5'Biotin + Spacer18 | dT(50)_18_TAGACGGGTCGACACGCGAGCGAATTCTAGACTGCAGGGCGGCCCTTGTT CAAGAT (SEQ ID NO: 24) |
| rs1041823:dT50_Y596_Y727_b02B | 5'Biotin + Spacer18 | dT(50)_18_TACGTTCCGGTAGCACGGTCCGAATTCTAGACTGCCACACGATAGTCATG GGGCTGT (SEQ ID NO: 25) |
| rs1468260:dT50_X596_X727_b01A | 5'Biotin + Spacer18 | dT(50)_18_TAGACGGGTCGACACGCGAGCGAATTCTAGACTGCAGGAGTAAGTCCCCA GCAAGGTG (SEQ ID NO: 26) |
| rs1468260:dT50_Y596_Y727_b02B | 5'Biotin + Spacer18 | dT(50)_18_TACGTTCCGGTAGCACGGTCCGAATTCTAGACTGCCACGGGGCCAGGTGA TATGTTC (SEQ ID NO: 27) |
| rs1898606:dT50_X596_X727_b01A | 5'Biotin + Spacer18 | dT(50)_18_TAGACGGGTCGACACGCGAGCGAATTCTAGACTGCAGGGGCAGTGTGTAA GGAAGACAGA (SEQ ID NO: 28) |
| rs1898606:dT50_Y596_Y727_b02B | 5'Biotin + Spacer18 | dT(50)_18_TACGTTCCGGTAGCACGGTCCGAATTCTAGACTGCCACAAGGGACTCCGT GTATGAAGAA (SEQ ID NO: 29) |

TABLE 1-continued

| Oligo Name | Chemistry | Oligo Sequence |
|---|---|---|
| rs721689:dT50_X596_X727_b01A | 5'Biotin + Spacer18 | dT(50)_18_TAGACGGGTCGACACGCGAGCGAATTCTAGACTGCAGGCACCCTCCCATG AACATTAT (SEQ ID NO: 30) |
| rs721689:dT50_Y596_Y727_b02B | 5'Biotin + Spacer18 | dT(50)_18_TACGTTCCGGTAGCACGGTCCGAATTCTAGACTGCCACTGTGTGTTGTGT TGGATGC (SEQ ID NO: 31) |
| rs1550538:dT50_X596_X727_b01A | 5'Biotin + Spacer18 | dT(50)_18_TAGACGGGTCGACACGCGAGCGAATTCTAGACTGCAGGGAGCAGGAAGAA CGGAATG (SEQ ID NO: 32) |
| rs1550538:dT50_Y596_Y727_b02B | 5'Biotin + Spacer18 | dT(50)_18_TACGTTCCGGTAGCACGGTCCGAATTCTAGACTGCCACATTCTCGACGGC TCACAAG (SEQ ID NO: 33) |
| rs1019982:dT50_X596_X727_b01A | 5'Biotin + Spacer18 | dT(50)_18_TAGACGGGTCGACACGCGAGCGAATTCTAGACTGCAGGCTGGATTCTGAG GTCACTTCTAC (SEQ ID NO: 34) |
| rs1019982:dT50_Y596_X727_b01B | 5'Biotin + Spacer18 | dT(50)_18_TACGTTCCGGTAGCACGGTCCGAATTCTAGACTGCCACCAACACAAGGCT TTTGCACTT (SEQ ID NO: 35) |
| rs2039078:dT50_X596_X727_b01A | 5'Biotin + Spacer | dT(50)_18_TAGACGGGTCGACACGCGAGCGAATTCTAGACTGCAGGCCCATCTTAGGT TCTGGGTCT (SEQ ID NO: 36) |
| rs2039078:dT50_Y596_Y727_bP2B | 5'Biotin + Spacer18 | dT(50)_18_TACGTTCCGGTAGCACGGTCCGAATTCTAGACTGCCACTGAGATATTCCT TTGGGCTCT (SEQ ID NO: 37) |
| rs2223114:dT50_X596_X727_b01A | 5'Biotin + Spacer18 | dT(50)_18_TAGACGGGTCGACACGCGAGCGAATTCTAGACTGCAGGTTGGCAATGTTG CAAGAAC (SEQ ID NO: 38) |
| rs2223114:dT50_Y596_Y727_b02B | 5'Biotin + Spacer18 | dT(50)_18_TACGTTCCGGTAGCACGGTCCGAATTCTAGACTGCCACCAAGCCTCGTCG TACTAATGA (SEQ ID NO: 39) |
| rs1478461:dT50_X596_X727_b01A | 5'Biotin + Spacer18 | dT(50)_18_TAGACGGGTCGACACGCGAGCGAATTCTAGACTGCAGGCCTGCACCAGTT TCCATCC (SEQ ID NO: 40) |
| rs1478461:dT50_Y596_Y727_b02B | 5'Biotin + Spacer18 | dT(50)_18_TACGTTCCGGTAGCACGGTCCGAATTCTAGACTGCCACAGTCTGGCAGGT CGGTTCT (SEQ ID NO: 41) |
| rs1871113:dT50_X596_X727_b01A | 5'Biotin + Spacer18 | dT(50)_18_TAGACGGGTCGACACGCGAGCGAATTCTAGACTGCAGGGCCATCGATGTT GACTTTAGA (SEQ ID NO: 42) |
| rs1871113:dT50_Y596_Y727_b02B | 5'Biotin + Spacer18 | dT(50)_18_TACGTTCCGGTAGCACGGTCCGAATTCTAGACTGCCACAAACAGCTGACA AACATTGGA (SEQ ID NO: 43) |
| Blocking oligos: | | |
| MPX:X2:xomp01A | 3'phosphate | ACTGGCCGTCGTTTTACAACCTGCAGTCTAGAATTCGCTC (SEQ ID NO: 44) |
| MPX:Y2:comp01B | 3'phosphate | GGTCATAGCTGTTTCCTGTGGCAGTCTAGAATTCGGAC (SEQ ID NO: 45) |
| Primers for pre-amplification: | | |
| KSG:rs4882913:b01A | 5'Biotin | gatgaatgcaacataagtctat (SEQ ID NO: 46) |
| AJB:rs6486847:b01A | 5'Biotin | agtatttcctggtattagggg (SEQ ID NO: 47) |
| KSG:rs10772596:b01A | 5'Biotin | gtcacaagcttattacatccta (SEQ ID NO: 48) |

TABLE 1-continued

| Oligo Name | Chemistry | Oligo Sequence |
| --- | --- | --- |
| KSG:nt8182473:B01A | 5'Biotin | aattatatgatgtggtgtctcc (SEQ ID NO: 49) |
| KSG:rs2377422:b01A | 5'Biotin | AACCCTAGGATATTACTGAGGA (SEQ ID NO: 50) |
| KSG:rs1894824:b01A | 5'Biotin | taacaatttctgtccttcagat (SEQ ID NO: 51) |
| KSG:rs12819884:b01A | 5'Biotin | ctggtcaaagaagatagagact (SEQ ID NO: 52) |
| KSG:rs1805721:b01A | 5'Biotin | gggttagagaaatgtgtaacaa (SEQ ID NO: 53) |
| KSG:rs4304840:b01A | 5'Biotin | gctgtagttttcatcttacttct (SEQ ID NO: 54) |
| KSG:rs1561560:b01A | 5'Biotin | cctaaagtttaaagtgctttcc (SEQ ID NO: 55) |
| KSG:rs1805731:b01A | 5'Biotin | ttttcagggaatgtatcttagg (SEQ ID NO: 56) |
| KSG:rs7300836:b01A | 5'Biotin | tatcacaggtcttttggttttt (SEQ ID NO: 57) |
| KSG:rs2580874:b01A | 5'Biotin | gtgttaggagagaggagatacc (SEQ ID NO: 58) |
| KSG:rs919209:b01A | 5'Biotin | gaagtagggaaaacactggttg (SEQ ID NO: 59) |
| KSG:rs4620776:b01A | 5'Biotin | TGTTCCAAAAAGAGATCTATGG (SEQ ID NO: 60) |
| KSG:rs7300097:b01A | 5'Biotin | atcaaacaccatacaaaaacca (SEQ ID NO: 61) |
| KSG:rs11046892:b01A | 5'Biotin | aactacacatcttgatcagctt (SEQ ID NO: 62) |
| KSG:rs2193005:b01A | 5'Biotin | aaagtcattaggtgagcaaaaa (SEQ ID NO: 63) |
| KSG:rs1805673:b01A | 5'Biotin | aagataatttggtgatccaacc (SEQ ID NO: 64) |
| KSG:rs11045985:b01A | 5'Biotin | acgtgagtactttctctccttt (SEQ ID NO: 65) |
| KSG:rs7310161:b01A | 5'Biotin | ctttcaacatcctagctccaac (SEQ ID NO: 66) |
| KSG:rs1805664:b01A | 5'Biotin | atgcatttaccttcccagatgt (SEQ ID NO: 67) |
| KSG:rs2075395:b01A | 5'Biotin | cttagcttctcaccaaaatgaa (SEQ ID NO: 68) |
| KSG:rs11046589:b01A | 5'Biotin | ttaacaagaaccatgccatttt (SEQ ID NO: 69) |
| KSG:rs2231754:b01A | 5'Biotin | tccattgcttctccagatcaaa (SEQ ID NO: 70) |
| KSG:rs4883146:b01A | 5'Biotin | agatgagctgctgataagttct (SEQ ID NO: 71) |
| KSG:rs226380:b01A | 5'Biotin | gggagtagggtacaatacagtct (SEQ ID NO: 72) |
| KSG:rs11057065:b01A | 5'Biotin | ctttcccaccaaggtcacaaaa (SEQ ID NO: 73) |
| KSG:rs1894814:b01A | 5'Biotin | cctccttcattagatccattaattt (SEQ ID NO: 74) |

TABLE 1-continued

| Oligo Name | Chemistry | Oligo Sequence |
|---|---|---|
| AJB:rs4604965:b01A | 5'Biotin | ttttggttctgaactcatccat (SEQ ID NO: 75) |
| KSG:rs10492115:b01A | 5'Biotin | catgcatgtcccaccacaatta (SEQ ID NO: 76) |
| AJB:rs7973072:b01A | 5'Biotin | tttcctactatgcccaaaccca (SEQ ID NO: 77) |
| KSG:rs7307991:b01A | 5'Biotin | aaagagagagagagaattttagcat (SEQ ID NO: 78) |
| KSG:rs3026251:b01A | 5'Biotin | ttacttgagaagtttagaggtgat (SEQ ID NO: 79) |
| KSG:rs3026252:b01A | 5'Biotin | gggtccaagtaggcaaagagac (SEQ ID NO: 80) |
| KSG:rs4882965:b01A | 5'Biotin | ctggaatcacacctcccccata (SEQ ID NO: 81) |
| KSG:rs7299659:b01A | 5'Biotin | taagccacactgAtgccttgac (SEQ ID NO: 82) |
| KSG:rs226389:b01A | 5'Biotin | catggaggctttagatggctca (SEQ ID NO: 83) |
| KSG:rs7134202:b01A | 5'Biotin | acggtctcttttgttcactggc (SEQ ID NO: 84) |
| KSG:rs1805750:b01A | 5'Biotin | tctcagttcccactaggccaaa (SEQ ID NO: 85) |
| KSG:rs2024301:b01A | 5'Biotin | CAGCTTCCAAGGAGAAGACTGC (SEQ ID NO: 86) |
| KSG:rs4883475:b01A | 5'Biotin | ccgcagaaatgcttcttccgtt (SEQ ID NO: 87) |
| KSG:rs2302516:b01A | 5'Biotin | gttgacccagagatcccccagg (SEQ ID NO: 88) |
| KSG:rs759052:b01A | 5'Biotin | caagtgagtTgccctgactgcc (SEQ ID NO: 89) |
| KSG:rs1133104:b01A | 5'Biotin | GTACTGGAGGCCCCCATTGTGC (SEQ ID NO: 90) |
| KSG:rs2110072:b01A | 5'Biotin | aagacctacatcgccagccagg (SEQ ID NO: 91) |
| KSG:rs2071079:b01A | 5'Biotin | cagTcctactgtgggtgcctgc (SEQ ID NO: 92) |
| KSG:rs226406:b01A | 5'Biotin | ccaTctcactcctagcttattc (SEQ ID NO: 93) |
| KSG:rs3741854:b01A | 5'Biotin | catcagcctctcttaaaatgt (SEQ ID NO: 94) |
| KSG:rs3809218:b01A | 5'Biotin | cccctagagaaacgatagactg (SEQ ID NO: 95) |
| KSG:rs4882913: - 01B | | tgcttccacacacaaatgtaat (SEQ ID NO: 96) |
| AJB:rs6486847: - 01B | | gaactctgttacatgcctcatt (SEQ ID NO: 97) |
| KSG:rs10772596: - 01B | | tactttagggatgagtgggaac (SEQ ID NO: 98) |
| KSG:nt8182473: - 01B | | agggatgaagagaaaaccagac (SEQ ID NO: 99) |
| KSG:rs2377422: - 01B | | ATTTCACTAAAACCATCCCTAA (SEQ ID NO: 100) |

TABLE 1-continued

| Oligo Name | Chemistry | Oligo Sequence |
|---|---|---|
| KSG:rs1894824: - 01B | | ataggcatacaacttttctgag (SEQ ID NO: 101) |
| KSG:rs12819884: - 01B | | agtctggcacaggtgtcttcag (SEQ ID NO: 102) |
| KSG:rs1805721: - 01B | | aggacattatgaggtattcaaa (SEQ ID NO: 103) |
| KSG:rs4304840: - 01B | | acaacttgcaataaaacagaca (SEQ ID NO: 104) |
| KSG:rs1561560: - 01B | | taaatgtctcccctcacgtaca (SEQ ID NO: 105) |
| KSG:rs1805731: - 01B | | aacctctgcatttattgtcagc (SEQ ID NO: 106) |
| KSG:rs7300836: - 01B | | cagttacagccatcagaaaact (SEQ ID NO: 107) |
| KSG:rs2580874: - 01B | | gggtttacataaacttctgccc (SEQ ID NO: 108) |
| KSG:rs919209: - 01B | | cacctgtgggaaatgaaggaaa (SEQ ID NO: 109) |
| KSG:rs4620776: - 01B | | GTAAAATCTGCAACTCTTCCTT (SEQ ID NO: 110) |
| KSG:rs7300097: - 01B | | gtttgattcattcgagacaaca (SEQ ID NO: 111) |
| KSG:rs11046892: - 01B | | agaggaaataatccaggcaagg (SEQ ID NO: 112) |
| KSG:rs2193005: - 01B | | gccatatacaatctttgagtag (SEQ ID NO: 113) |
| KSG:rs1805673: - 01B | | gaggaaagtttacagaaacagt (SEQ ID NO: 114) |
| KSG:rs11045985: - 01B | | taattccatctgcttctttgaa (SEQ ID NO: 115) |
| KSG:rs7310161: - 01B | | gcagggccacagcaggttagac (SEQ ID NO: 116) |
| KSG:rs1805664: - 01B | | agagaacttccagtctatttgc (SEQ ID NO: 117) |
| KSG:rs2075395: - 01B | | agagtggaagacaccgttgtaa (SEQ ID NO: 118) |
| KSG:rs11046589: - 01B | | cccgctacagatgaaacaggta (SEQ ID NO: 119) |
| KSG:rs2231754: - 01B | | ggtgtaggagatatgtacagtcaat (SEQ ID NO: 120) |
| KSG:rs4883146: - 01B | | agcctaagttagtgtccccaag (SEQ ID NO: 121) |
| KSG:rs226380: - 01B | | cagaaagaaggagctggaggag (SEQ ID NO: 122) |
| KSG:rs11057065: - 01B | | ggttgaattagttgaccctgac (SEQ ID NO: 123) |
| KSG:rs1894814: - 01B | | cagacaggcagtgagcagaggg (SEQ ID NO: 124) |
| AJB:rs4604965: - 01B | | gtagtagcaatttgtttggtga (SEQ ID NO: 125) |
| KSG:rs10492115: - 01B | | tctttgatacacggcaaggtgc (SEQ ID NO: 126) |

TABLE 1-continued

| Oligo Name | Chemistry | Oligo Sequence |
|---|---|---|
| AJB:rs7973072: - 01B | | ccaaaaagggtttctattttag<br>(SEQ ID NO: 127) |
| KSG:rs7307991: - 01B | | taacaagtccgtAgggtttccat<br>(SEQ ID NO: 128) |
| KSG:rs3026251: - 01B | | aattctggctggagAtgggaag<br>(SEQ ID NO: 129) |
| KSG:rs3026252: - 01B | | acatttatgggctctgctctta<br>(SEQ ID NO: 130) |
| KSG:rs4882965: - 01B | | gatgcttccaatttagagacaa<br>(SEQ ID NO: 131) |
| KSG:rs7299659: - 01B | | gaataggcccctctctctggtc<br>(SEQ ID NO: 132) |
| KSG:rs226389: - 01B | | gtgagtgtttcagaacgataga<br>(SEQ ID NO: 133) |
| KSG:rs7134202: - 01B | | aagtcagatcttgctctatgtg<br>(SEQ ID NO: 134) |
| KSG:rs1805850: - 01B | | gggaaggatatcgcatcttaaa<br>(SEQ ID NO: 135) |
| KSG:rs2024301: - 01B | | TGGGGAATCCGGTATTACTTTT<br>(SEQ ID NO: 136) |
| KSG:rs4883475: - 01B | | tctcatctggggaaagactgtg<br>(SEQ ID NO: 137) |
| KSG:rs2302516: - 01B | | agacagcttggtggggatacac<br>(SEQ ID NO: 138) |
| KSG:rs759052: - 01B | | ggacaaagggtggatgccggg<br>(SEQ ID NO: 139) |
| KSG:rs1133104: - 01B | | CCGGATAAAAATTAAGAGAGACTCA<br>(SEQ ID NO: 140) |
| KSG:rs2110072: - 01B | | tcattgaccgtggcctcAagac<br>(SEQ ID NO: 141) |
| KSG:rs2071079: - 01B | | gcccaagctagtcaggTcaagg<br>(SEQ ID NO: 142) |
| KSG:rs226406: - 01B | | tctttgaggaggaaatatgttg<br>(SEQ ID NO: 143) |
| KSG:rs3741854: - 01B | | gtaagggcttcaaaggaatgc<br>(SEQ ID NO: 144) |
| KSG:rs3809218: - 01B | | ttgaggtgagggattaaacaat<br>(SEQ ID NO: 145) |
| 50 MegaPlex assays: | | |
| MPX:T10:X2:rs4882913:b01A | 5'biotin | dT(10)GAGCGAATTCTAGACTGCAGGTTGTAAAACGACGGCCAGTgatgaatgcaacat<br>aagtctat<br>(SEQ ID NO: 146) |
| MPX:T10:Y2:rs4882913:b01B | 5'biotin | dT(10)GTCCGAATTCTAGACTGCCACAGGAAACAGCTATGACCtgcttccacacacaaa<br>tgtaat<br>(SEQ ID NO: 147) |
| MPX:T10:X2:rs6486847:b01A | 5'biotin | dT(10)GAGCGAATTCTAGACTGCAGGTTGTAAAACGACGGCCAGTagtattttcctggt<br>attagggg<br>(SEQ ID NO: 148) |
| MPX:T10:Y2:rs6486847:b01B | 5'biotin | dT(10)GTCCGAATTCTAGACTGCCACAGGAAACAGCTATGACCgaactctgttacatgc<br>ctcatt<br>(SEQ ID NO: 149) |
| MPX:T10:X2:rs10772596:b01A | 5'biotin | dT(10)GAGCGAATTCTAGACTGCAGGTTGTAAAACGACGGCCAGTgtcacaagcttatt<br>acatccta<br>(SEQ ID NO: 150) |

TABLE 1-continued

| Oligo Name | Chemistry | Oligo Sequence |
| --- | --- | --- |
| MPX:T10:Y2:rs10772596:b10B | 5'biotin | dT(10)GTCCGAATTCTAGACTGCCACAGGAAACAGCTATGACCtactttagggatgagt<br>gggaac<br>(SEQ ID NO: 151) |
| MPX:T10:X2:rs10840759:b10A | 5'biotin | dT(10)GAGCGAATTCTAGACTGCAGGTTGTAAAACGACGGCCAGTaattatatgatgtg<br>gtgtctcc<br>(SEQ ID NO: 152) |
| MPX:T10:Y2:rs10840759:b10B | 5'biotin | dT(10)GTCCGAATTCTAGACTGCCACAGGAAACAGCTATGACCagggatgaagagaaaa<br>ccagac<br>(SEQ ID NO: 153) |
| MPX:T10:X2:rs2377422:b01A | 5'biotin | dT(10)GAGCGAATTCTAGACTCGAGGTTGTAAAACGACGGCCAGTAACCCTAGGATATT<br>ACTGAGGA<br>(SEQ ID NO: 154) |
| MPX:T10:Y2:rs2377422:b01B | 5'biotin | dT(10)GTCCGAATTCAGACTGCCACAGGAAACAGCTATGACCATTTCACTAAAACCATC<br>CCTAA<br>(SEQ ID NO: 155) |
| MPX:T10:X2:rs1894824:b01A | 5'biotin | dT(10)GAGCGAATTCTAGACTGCAGGTTGTAAAACGACGGCCAGTtaacaatttctgtc<br>cttcagat<br>(SEQ ID NO: 156) |
| MPX:T10:Y2:rs1894824:b01B | 5'biotin | dT(10)GTCCGAATTCTAGACTGCCACAGGAAACAGCTATGACCataggcatacaacttt<br>tctgag<br>(SEQ ID NO: 157) |
| MPX:T10:X2:rs12819884:b01A | 5'biotin | dT(10)GAGCGAATTCTAGACTGCAGGTTGTAAAACGACGGCCAGTctggtcaaagaaga<br>tagagact<br>(SEQ ID NO: 158) |
| MPX:T10:Y2:rs12819884:b01B | 5'biotin | dT(10)GTCCGAATTCTAGACTGCCACAGGAAACAGCTATGACCagtctggcacaggtgt<br>cttcag<br>(SEQ ID NO: 159) |
| MPX:T10:X2:rs1805721:b01A | 5'biotin | dT(10)GAGCGAATTCTAGACTGCAGGTTGTAAAACGACGGCCAGTgggttagagaaatg<br>tgtaacaa<br>(SEQ ID NO: 160) |
| MPX:T10:Y2:rs1805721:b01B | 5'biotin | dT(10)GTCCGAATTCTAGACTGCCACAGGAAACAGCTATGACCaggacattatgaggta<br>ttcaaa<br>(SEQ ID NO: 161) |
| MPX:T10:X2:rs4304840:b01A | 5'biotin | dT(10)GAGCGAATTCTAGACTGCAGGTTGTAAAACGACGGCCAGTgctgtagttttcat<br>cttacttct<br>(SEQ ID NO: 162) |
| MPX:T10:Y2:rs4304840:b01B | 5'biotin | dT(10)GTCCGAATTCTAGACTGCCACAGGAAACAGCTATGACCacaacttgcaataaac<br>agaca<br>(SEQ ID NO: 163) |
| MPX:T10:X2:rs1561560:b01A | 5'biotin | dT(10)GAGCGAATTCTAGACTGCAGGTTGTAAAACGACGGCCAGTcctaaagtttaaag<br>tgctttcc<br>(SEQ ID NO: 164) |
| MPX:T10:Y2:rs1561560:b01B | 5'biotin | dT(10)GTCCGAATTCTAGACTGCCACAGGAAACAGCTATGACCtaaatgtctcccctca<br>cgtaca<br>(SEQ ID NO: 165) |
| MPX:T10:X2:rs1805731:b01A | 5'biotin | dT(10)GAGCGAATTCTAGACTGCAGGTTGTAAAACGACGGCCAGTttttcagggaatgt<br>atcttagg<br>(SEQ ID NO: 166) |
| MPX:T10:Y2:rs1805731:b01B | 5'biotin | dT(10)GTCCGAATTCTAGACTGCCACAGGAAACAGCTATGACCaacctctgcatttatt<br>gtcagc<br>(SEQ ID NO: 167) |
| MPX:T10:X2:rs7300836:b01A | 5'biotin | dT(10)GAGCGAATTCTAGACTGCAGGTTGTAAAACGACGGCCAGTtatcacaggtcttt<br>tggttttt<br>(SEQ ID NO: 168) |
| MPX:T10:Y2:rs7300836:b01B | 5'biotin | dT(10)GTCCGAATTCTAGACTGCCACAGGAAACAGCTATGACCcagttacagccatcag<br>aaaact<br>(SEQ ID NO: 169) |

TABLE 1-continued

| Oligo Name | Chemistry | Oligo Sequence |
|---|---|---|
| MPX:T10:X2:rs2580874:b01A | 5'biotin | dT(10)GAGCGAATTCTAGACTGCAGGTTGTAAAACGACGGCCAGTgtgttaggagagag gagatacc<br>(SEQ ID NO: 170) |
| MPX:T10:Y2:rs2580874:b01B | 5'biotin | dT(10)GTCCGAATTCTAGACTGCCACAGGAAACAGCTATGACCgggtttacataaactt ctgccc<br>(SEQ ID NO: 171) |
| MPX:T10:X2:rs919209:b01A | 5'biotin | dT(10)GAGCGAATTCTAGACTGCAGGTTGTAAAACGACGGCCAGTgaagtagggaaaac actggttg<br>(SEQ ID NO: 172) |
| MPX:T10:Y2:rs919209:b10B | 5'biotin | dT(10)GTCCGAATTCTAGACTGCCACAGGAAACAGCTATGACCcacctgtgggaaatga aggaaa<br>(SEQ ID NO: 173) |
| MPX:T10:X2:rs4620776:b01A | 5'biotin | dT(10)GAGCGAATTCTAGACTGCAGGTTGTAAAACGACGGCCAGTTGTTCCAAAAAGAG ATCTATGG<br>(SEQ ID NO: 174) |
| MPX:T10:Y2:rs4620776:b01B | 5'biotin | dT(10)GTCCGAATTCTAGACTGCCACAGGAAACAGCTATGACCGTAAAAATCTGCAACT CTTCCTT<br>(SEQ ID NO: 175) |
| MPX:T10:X2:rs7300097:b01A | 5'biotin | dT(10)GAGCGAATTCTAGACTGCAGGTTGTAAAACGACGGCCAGTatcaaacaccatac aaaaacca<br>(SEQ ID NO: 176) |
| MPX:T10:Y2:rs7300097:b01B | 5'biotin | dT(10)GTCCGAATTCTAGACTGCCACAGGAAACAGCTATGACCgtttgattcattcgag acaaca<br>(SEQ ID NO: 177) |
| MPX:T10:X2:rs11046892:b01A | 5'biotin | dT(10)GAGCGAATTCTAGACTGCAGGTTGTAAAACGACGGCCAGTaactacacatcttg atcagctt<br>(SEQ ID NO: 178) |
| MPX:T10:Y2:rs11046892:b01B | 5'biotin | dT(10)GTCCGAATTCTAGACTGCCACAGGAAACAGCTATGACCagaggaaataatccag gcaagg<br>(SEQ ID NO: 179) |
| MPX:T10:X2:rs2193005:b01A | 5'biotin | dT(10)GAGCGAATTCTAGACTGCAGGTTGTAAAACGACGGCCAGTaaagtcattaggtg agcaaaaa<br>(SEQ ID NO: 180) |
| MPX:T10:Y2:rs2193005:b01B | 5'biotin | dT(10)GTCCGAATTCTAGACTGCCACAGGAAACAGCTATGACCgccatatacaatcttt gagtag<br>(SEQ ID NO: 181) |
| MPX:T10:X2:rs1805673:b01A | 5'biotin | dT(10)GAGCGAATTCTAGACTGCAGGTTGTAAAACGACGGCCAGTaagataatttggtg atccaacc<br>(SEQ ID NO: 182) |
| MPX:T10:Y2:rs1805673:b01B | 5'biotin | dT(10)GTCCGAATTCTAGACTGCCACAGGAAACAGCTATGACCgaggaaagtttacaga aacagt<br>(SEQ ID NO: 183) |
| MPX:T10:X2:rs11045985:b01A | 5'biotin | dT(10)GAGCGAATTCTAGACTGCAGGTTGTAAAACGACGGCCAGTacgtgagtactttc tctcctt<br>(SEQ ID NO: 184) |
| MPX:T10:Y2:rs11045985:b01B | 5'biotin | dT(10)GTCCGAATTCTAGACTGCCACAGGAAACAGCTATGACCtaattccatctgcttc tttgaa<br>(SEQ ID NO: 185) |
| MPX:T10:X2:rs7310161:b01A | 5'biotin | dT(10)GAGCGAATTCTAGACTGCAGGTTGTAAAACGACGGCCAGTctttcaacatccta gctccaac<br>(SEQ ID NO: 186) |
| MPX:T10:Y2:rs7310161:b01B | 5'biotin | dT(10)GTCCGAATTCTAGACTGCCACAGGAAACAGCTATGACCgcagggccacagcagg ttagac<br>(SEQ ID NO: 187) |
| MPX:T10:X2:rs1805664:b01A | 5'biotin | dT(10)GAGCGAATTCTAGACTGCAGGTTGTAAAACGACGGCCAGTatgcatttaccttc ccagatgt<br>(SEQ ID NO: 188) |

TABLE 1-continued

| Oligo Name | Chemistry | Oligo Sequence |
|---|---|---|
| MPX:T10:Y2:rs1805664:b01B | 5'biotin | dT(10)GTCCGAATTCTAGACTGCCACAGGAAACAGCTATGACCagagaacttccagtct atttgc<br>(SEQ ID NO: 189) |
| MPX:T10:X2:rs2075395:b01A | 5'biotin | dT(10)GAGCGAATTCTAGACTGCAGGTTGTAAAACGACGGCCAGTcttagcttctcacc aaaatgaa<br>(SEQ ID NO: 190) |
| MPX:T10:Y2:rs2075395:b01B | 5'biotin | dT(10)GTCCGAATTCTAGACTGCCACAGGAAACAGCTATGACCagagtggaagacaccg ttgtaa<br>(SEQ ID NO: 191) |
| MPX:T10:X2:rs11046589:b01A | 5'biotin | dT(10)GAGCGAATTCTAGACTGCAGGTTGTAAAACGACGGCCAGTttaacaagaaccat gccatttt<br>(SEQ ID NO: 192) |
| MPX:T10:Y2:rs11046589:b01B | 5'biotin | dT(10)GTCCGAATTCTAGACTGCCACAGGAAACAGCTATGACCcccgctacagatgaaa caggta<br>(SEQ ID NO: 193) |
| MPX:T10:X2:rs2231754:b01A | 5'biotin | dT(10)GAGCGAATTCTAGACTGCAGGTTGTAAAACGACGGCCAGTtccattgcttctcc agatcaaa<br>(SEQ ID NO: 194) |
| MPX:T10:Y2:rs2231754:b01B | 5'biotin | dT(10)GTCCGAATTCTAGACTGCCACAGGAAACAGCTATGACCggtgtaggagatatgt acagtcaat<br>(SEQ ID NO: 195) |
| MPX:T10:X2:rs4883146:b01A | 5'biotin | dT(10)GAGCGAATTCTAGACTGCAGGTTGTAAAACGACGGCCAGTagatgagctgctga taagttct<br>(SEQ ID NO: 196) |
| MPX:T10:Y2:rs4883146:b01B | 5'biotin | dT(10)GTCCGAATTCTAGACTGCCACAGGAAACAGCTATGACCagcctaagttagtgtc cccaag<br>(SEQ ID NO: 197) |
| MPX:T10:X2:rs226380:b01A | 5'biotin | dT(10)GAGCGAATTCTAGACTGCAGGTTGTAAAACGACGGCCAGTgggagtagggtaca atacagtct<br>(SEQ ID NO: 198) |
| MPX:T10:Y2:rs226380:b01B | 5'biotin | dT(10)GTCCGAATTCTAGACTGCCACAGGAAACAGCTATGACCcagaaagaaggagctg gaggag<br>(SEQ ID NO: 199) |
| MPX:T10:X2:rs1105706:b01A | 5'biotin | dT(10)GAGCGAATTCTAGACTGCAGGTTGTAAAACGACGGCCAGTctttcccaccaagg tcacaaa<br>(SEQ ID NO: 200) |
| MPX:T10:Y2:rs1105706:b01B | 5'biotin | dT(10)GTCCGAATTCTAGACTGCCACAGGAAACAGCTATGACCggttgaattagttgac cctgac<br>(SEQ ID NO: 201) |
| MPX:T10:X2:rs1894814:b01A | 5'biotin | dT(10)GAGCGAATTCTAGACTGCAGGTTGTAAAACGACGGCCAGTcctccttcattaga tccattaattt<br>(SEQ ID NO: 202) |
| MPX:T10:Y2:rs1894814:b01B | 5'biotin | dT(10)GTCCGAATTCTAGACTGCCACAGGAAACAGCTATGACCcagacaggcagtgagc agaggg<br>(SEQ ID NO: 203) |
| MPX:T10:X2:rs4604965:b01A | 5'biotin | dT(10)GAGCGAATTCTAGACTGCAGGTTGTAAAACGACGGCCAGTttttggttctgaac tcatccat<br>(SEQ ID NO: 204) |
| MPX:T10:Y2:rs4604965:b01B | 5'biotin | dT(10)GTCCGAATTCTAGACTGCCACAGGAAACAGCTATGACCgtagtagcaatttgtt tggtga<br>(SEQ ID NO: 205) |
| MPX:T10:X2:rs10492115:b01A | 5'biotin | dT(10)GAGCGAATTCTAGACTGCAGGTTGTAAAACGACGGCCAGTcatgcatgtcccac cacaatta<br>(SEQ ID NO: 206) |
| MPX:T10:Y2:rs10492115:b01B | 5'biotin | dT(10)GTCCGAATTCTAGACTGCCACAGGAAACAGCTATGACCtctttgatacacggca aggtgc<br>(SEQ ID NO: 207) |

TABLE 1-continued

| Oligo Name | Chemistry | Oligo Sequence |
| --- | --- | --- |
| MPX:T10:X2:rs7973072:b01A | 5'biotin | dT(10)GAGCGAATTCTAGACTGCAGGTTGTAAAACGACGGCCAGTttttcctactatgcc caaaccca (SEQ ID NO: 208) |
| MPX:T10:Y2:rs7973072:b01B | 5'biotin | dT(10)GTCCGAATTCTAGACTGCCACAGGAAACAGCTATGACCcccaaaaagggtttcta ttttag (SEQ ID NO: 209) |
| MPX:T10:X2:rs7307991:b01A | 5'biotin | dT(10)GAGCGAATTCTAGACTGCAGGTTGTAAAACGACGGCCAGTaaagagagagagag aattttagcat (SEQ ID NO: 210) |
| MPX:T10:Y2:rs7307991:b01B | 5'biotin | dT(10)GTCCGAATTCTAGACTGCCACAGGAAACAGCTATGACCtaacaagtccgtAggg tttccat (SEQ ID NO: 211) |
| MPX:T10:X2:rs3026251:b01A | 5'biotin | dT(10)GAGCGAATTCTAGACTGCAGGTTGTAAAACGACGGCCAGTttaccttgagaagt ttagaggtgat (SEQ ID NO: 212) |
| MPX:T10:Y2:rs3026251:b01B | 5'biotin | dT(10)GTCCGAATTCTAGACTGCCACAGGAAACAGCTATGACCaattctggctggagAt gggaag (SEQ ID NO: 213) |
| MPX:T10:X2:rs3026252:b01A | 5'biotin | dT(10)GAGCGAATTCTAGACTGCAGGTTGTAAAACGACGGCCAGTgggtccaagtaggc aaagagac (SEQ ID NO: 214) |
| MPX:T10:Y2:rs3026252:b01B | 5'biotin | dT(10)GTCCGAATTCTAGACTGCCACAGGAAACAGCTATGACCacatttatgggctctg ctctta (SEQ ID NO: 215) |
| MPX:T10:X2:rs4882965:b01A | 5'biotin | dT(10)GAGCGAATTCTAGACTGCAGGTTGTAAAACGACGGCCAGTctggaatcacacct cccccata (SEQ ID NO: 216) |
| MPX:T10:Y2:rs4882965:b01B | 5'biotin | dT(10)GTCCGAATTCTAGACTGCCACAGGAAACAGCTATGACCgatgcttccaatttag agacaa (SEQ ID NO: 217) |
| MPX:T10:X2:rs7299659:b01A | 5'biotin | dT(10)GAGCGAATTCTAGACTGCAGGTTGTAAAACGACGGCCAGTtaagccacactgAt gccttgac (SEQ ID NO: 218) |
| MPX:T10:Y2:rs7299659:b01B | 5'biotin | dT(10)GTCCGAATTCTAGACTGCCACAGGAAACAGCTATGACCgaataggcccctctct ctggtc (SEQ ID NO: 219) |
| MPX:T10:X2:rs226389:b01A | 5'biotin | dT(10)GAGCGAATTCTAGACTGCAGGTTGTAAAACGACGGCCAGTcatggaggctttag tggctca (SEQ ID NO: 220) |
| MPX:T10:Y2:rs226839:b01B | 5'biotin | dT(10)GTCCGAATTCTAGACTGCCACAGGAAACAGCTATGACCgtgagtgtttcagaac gataga (SEQ ID NO: 221) |
| MPX:T10:X2:rs7134202:b01A | 5'biotin | dT(10)GAGCGAATTCTAGACTGCAGGTTGTAAAACGACGGCCAGTacggtctcttttgt tcactggc (SEQ ID NO: 222) |
| MPX:T10:Y2:rs7134202:b01B | 5'biotin | dT(10)GTCCGAATTCTAGACTGCCACAGGAAACAGCTATGACCaagtcagatcttgctc tatgt (SEQ ID NO: 223) |
| MPX:T10:X2:rs1805750:b01A | 5'biotin | dT(10)GAGCGAATTCTAGACTGCAGGTTGTAAAACGACGGCCAGTtctcagttcccact aggccaaa (SEQ ID NO: 224) |
| MPX:T10:Y2:rs1805750:b01B | 5'biotin | dT(10)GTCCGAATTCTAGACTGCCACAGGAAACAGCTATGACCgggaaggatatcgcat cttaaa (SEQ ID NO: 225) |
| MPX:T10:X2:rs2024301:b01A | 5'biotin | dT(10)GAGCGAATTCTAGACTGCAGGTTGTAAAACGACGGCCAGTCAGCTTCCAAGGAG AAGACTGC (SEQ ID NO: 226) |

TABLE 1-continued

| Oligo Name | Chemistry | Oligo Sequence |
|---|---|---|
| MPX:T10:Y2:rs2024301:b10B | 5'biotin | dT(10)GTCCGAATTCTAGACTGCCACAGGAAACAGCTATGACCTGGGGAATCCGGTATT ACTTTT (SEQ ID NO: 227) |
| MPX:T10:X2:rs4883475:b01A | 5'biotin | dT(10)GAGCGAATTCTAGACTGCAGGTTGTAAAACGACGGCCAGTccgcagaaatgctt cttccgtt (SEQ ID NO: 228) |
| MPX:T10:Y2:rs4883475:b01B | 5'biotin | dT(10)GTCCGAATTCTAGACTGCCACAGGAAACAGCTATGACCtctcatctggggaaag actgtg (SEQ ID NO: 229) |
| MPX:T10:X2:rs2302516:b01A | 5'biotin | dT(10)GAGCGAATTCTAGACTGCAGGTTGTAAAACGACGGCCAGTgttgacccagagatc ccccagg (SEQ ID NO: 230) |
| MPX:T10:Y2:rs2302516:b01B | 5'biotin | dT(10)GTCCGAATTCTAGACTGCCACAGGAAACAGCTATGACCagacagcttggtgggg atacac (SEQ ID NO: 231) |
| MPX:T10:X2:rs759052:b01A | 5'biotin | dT(10)GAGCGAATTCTAGACTGCAGGTTGTAAAACGACGGCCAGTcaagtgagtTgccc tgactgcc (SEQ ID NO: 232) |
| MPX:T10:Y2:rs759052:b01B | 5'biotin | dT(10)GTCCGAATTCTAGACTGCCACAGGAAACAGCTATGACCggacaaaggggtggat gccggg (SEQ ID NO: 233) |
| MPX:T10:X2:rs1133104:b01A | 5'biotin | dT(10)GAGCGAATTCTAGACTGCAGGTTGTAAAACGACGGCCAGTGTACTGGAGGCCCC CATTGTGC (SEQ ID NO: 234) |
| MPX:T10:Y2:rs1133104:b01B | 5'biotin | dT(10)GTCCGAATTCTAGACTGCCACAGGAAACAGCTATGACCCCGGATAAAAATTAAG AGAGACTCA (SEQ ID NO: 235) |
| MPX:T10:X2:rs110072:b01A | 5'biotin | dT(10)GAGCGAATTCTAGACTGCAGGTTGTAAAACGACGGCCAGTaagacctacatcgc cagccagg (SEQ ID NO: 236) |
| MPX:T10:Y2:rs110072:b01B | 5'biotin | dT(10)GTCCGAATTCTAGACTGCCACAGGAAACAGCTATGACCtcattgaccgtggcct cAagac (SEQ ID NO: 237) |
| MPX:T10:X2:rs2071078:b01A | 5'biotin | dT(10)GAGCGAATTCTAGACTGCAGGTTGTAAAACGACGGCCAGTcagTcctactgtgg gtgcctgc (SEQ ID NO: 238) |
| MPX:T10:Y2:rs2071078:b01B | 5'biotin | dT(10)GTCCGAATTCTAGACTGCCACAGGAAACAGCTATGACCgcccaagctagtcagg Tcaagg (SEQ ID NO: 239) |
| MPX:T10:X2:rs226406:b01A | 5'biotin | dT(10)GAGCGAATTCTAGACTGCAGGTTGTAAAACGACGGCCAGTccaTctcactccta gcttattc (SEQ ID NO: 240) |
| MPX:T10:Y2:rs226406:b01B | 5'biotin | dT(10)GTCCGAATTCTAGACTGCCACAGGAAACAGCTATGACCtctttgaggaggaaat atgttg (SEQ ID NO: 241) |
| MPX:T10:X2:rs3741854:b01A | 5'biotin | dT(10)GAGCGAATTCTAGACTGCAGGTTGTAAAACGACGGCCAGTcatcagcctctctt taaaatgt (SEQ ID NO: 242) |
| MPX:T10:Y2:rs3741854:b01B | 5'biotin | dT(10)GTCCGAATTCTAGACTGCCACAGGAAACAGCTATGACCgtaaggggcttcaaag gaatgc (SEQ ID NO: 243) |
| MPX:T10:X2:rs3809218:b01A | 5'biotin | dT(10)GAGCGAATTCTAGACTGCAGGTTGTAAAACGACGGCCAGTcccctagagaaacg atagactg (SEQ ID NO: 244) |
| MPX:T10:Y2:rs3809218:b01B | 5'biotin | dT(10)GTCCGAATTCTAGACTGCCACAGGAAACAGCTATGACCttgaggtgagggatta aacaat (SEQ ID NO: 245) |

REFERENCES

Adessi, C. et al. (2000) Nucl. Acids Res. 28 (20): e87-.
Bing, D. H. et al. (1996). Bridge Amplification: A Solid Phase PCR System for the Amplification and Detection of Allelic Differences in Single Copy Genes. Seventh International Symposium on Human Identification.
Broude, N. E. et al. (2001) PNAS 98(1): 206-211.
Brownie, J. et al. (1997) Nucl. Acids Res. 25(16): 3235-3241.
Dahl, F. et al. (2005) Nucl. Acids Res. 33 (8): e71-.
Li, D. and J. Vijg (1996) Nucl. Acids Res. 24(3): 538-539.
Lin, Z. et al. (1996) PNAS 93(6): 2582-2587.
Meuzelaar et al (2007) Nat. Meths. 4 (10) 835-837
Pemov, A. et al. (2005) Nucl. Acids Res. 33 (2): e11-.
Shapero, M. H. et al. (2004) Nucl. Acids Res. 32 (22): e181-.
Tillib, S. V. et al. (2001). Analytical Biochemistry 292(1): 155-160.

---

The invention claimed is:

1. A method of amplifying one or more target regions in a nucleic acid sample comprising;
   (i) providing forward and reverse compound primers immobilised on the surface of a solid support, wherein said forward and reverse compound primers comprise a common amplification sequence and a specific primer sequence, the specific primer sequences of the immobilised forward and reverse compound primers being hybridisable to the one or more target regions of the nucleic acid sample,
   (ii) hybridising a non-priming barrier oligonucleotide to the common sequences of the immobilised forward and reverse compound primers,
   (iii) hybridising a template strand of the nucleic acid sample to the specific primer sequence of the forward compound primers,
   (iv) extending the forward compound primers along the template strand to produce immobilised first extension products comprising the compound primer and the complementary sequence of the one or more target regions of the template strand of the nucleic acid sample,
   (v) hybridising the first extension products to the immobilised reverse compound primers,
   (vi) extending the reverse compound primers along the first extension products to produce immobilised second extension products comprising the sequence of the reverse compound primer, the template strand of the nucleic acid sample in the target region and the complement of the forward compound primer, and,
   (vii) amplifying the immobilised second extension products using common primers which hybridise to the complement of the common sequences of the forward and reverse compound primers to produce amplified nucleic acid molecules in solution which comprise the one or more target regions.

2. A method according to claim 1 comprising, following step (vi), treating the 3' ends of non-extended primers on the surface of the solid support to prevent priming from said primers.

3. A method according to claim 2 wherein said primers are treated by addition of ddATP to the 3'-end.

4. A method according to claim 1 wherein the forward and reverse compound primers are immobilised in a discrete zone on the surface of a solid support.

5. A method according to claim 1 comprising washing, and, optionally, recovering the template strand following step (iv).

6. A method according to claim 1 comprising washing the immobilised extension products following step (vi).

7. A method according to claim 4 wherein at least 10 different pairs of forward and reverse compound primers are immobilised in discrete zones on the surface of the solid support, each pair of forward and reverse compound primers being suitable for amplifying a different target region of said DNA sample.

8. A method according to claim 1 wherein the compound primers are immobilised on the surface via a spacer.

9. A method according to claim 1 comprising the initial step of enriching the nucleic acid sample for the one or more target regions by pre-amplification in solution using amplification primers specific for the one or more target regions, to produce a nucleic acid sample enriched for the one or more target regions.

10. A method according to claim 1 wherein step (vii) comprises;
   amplifying the immobilised second extension products using a first pair of common primers which hybridise to the complement of the common sequences of the forward and reverse compound primers to produce first amplified nucleic acid molecules in solution, and,
   amplifying the first amplified nucleic acid molecules using a second pair of nested common primers to produce second amplified nucleic acid molecules in solution which comprise the one or more target regions.

* * * * *

SEQUENCE LISTING

```
<160> NUMBER OF SEQ ID NOS: 247

<210> SEQ ID NO 1
<211> LENGTH: 50
<212> TYPE: DNA
<213> ORGANISM: Artificial sequence
<220> FEATURE:
<223> OTHER INFORMATION: Synthetic sequence: Oligonucleotide

<400> SEQUENCE: 1
tttttttttu gagcgaattc tagactgcag gctgcatttt ggcacaaccc            50

<210> SEQ ID NO 2
<211> LENGTH: 52
<212> TYPE: DNA
<213> ORGANISM: Artificial sequence
<220> FEATURE:
<223> OTHER INFORMATION: Synthetic sequence: Oligonucleotide

<400> SEQUENCE: 2
tttttttttt gagcgaattc tagactgcag ggtttcattc ctgtttgtca gt         52

<210> SEQ ID NO 3
<211> LENGTH: 50
<212> TYPE: DNA
<213> ORGANISM: Artificial sequence
<220> FEATURE:
<223> OTHER INFORMATION: Synthetic sequence: Oligonucleotide

<400> SEQUENCE: 3
gtttcattcc tgtttgtcag ttgtacggtg ggttgtgcca aaatgcagtt            50

<210> SEQ ID NO 4
<211> LENGTH: 17
<212> TYPE: DNA
<213> ORGANISM: Artificial sequence
<220> FEATURE:
<223> OTHER INFORMATION: Synthetic sequence: Oligonucleotide

<400> SEQUENCE: 4
cagttgtacg gtgggtt                                                17

<210> SEQ ID NO 5
<211> LENGTH: 17
<212> TYPE: DNA
<213> ORGANISM: Artificial sequence
<220> FEATURE:
<223> OTHER INFORMATION: Synthetic sequence: Oligonucleotide

<400> SEQUENCE: 5
aacccaccgt acaactg                                                17

<210> SEQ ID NO 6
<211> LENGTH: 21
<212> TYPE: DNA
```

```
<213> ORGANISM: Artificial sequence
<220> FEATURE:
<223> OTHER INFORMATION: Synthetic sequence: Oligonucleotide

<400> SEQUENCE: 6
gagcgaattc tagactgcag g                                              21

<210> SEQ ID NO 7
<211> LENGTH: 21
<212> TYPE: DNA
<213> ORGANISM: Artificial sequence
<220> FEATURE:
<223> OTHER INFORMATION: Synthetic sequence: Oligonucleotide

<400> SEQUENCE: 7
gtccgaattc tagactgcca c                                              21

<210> SEQ ID NO 8
<211> LENGTH: 21
<212> TYPE: DNA
<213> ORGANISM: Artificial sequence
<220> FEATURE:
<223> OTHER INFORMATION: Synthetic sequence: Oligonucleotide

<400> SEQUENCE: 8
tagacgggtc gacacgcgag c                                              21

<210> SEQ ID NO 9
<211> LENGTH: 21
<212> TYPE: DNA
<213> ORGANISM: Artificial sequence
<220> FEATURE:
<223> OTHER INFORMATION: Synthetic sequence: Oligonucleotide

<400> SEQUENCE: 9
tacgttccgg tagcacggtc c                                              21

<210> SEQ ID NO 10
<211> LENGTH: 20
<212> TYPE: DNA
<213> ORGANISM: Artificial sequence
<220> FEATURE:
<223> OTHER INFORMATION: Synthetic sequence: Oligonucleotide

<400> SEQUENCE: 10
gttgtaaaac gacggccagt                                                20

<210> SEQ ID NO 11
<211> LENGTH: 20
<212> TYPE: DNA
<213> ORGANISM: Artificial sequence
<220> FEATURE:
<223> OTHER INFORMATION: Synthetic sequence: Oligonucleotide

<400> SEQUENCE: 11
cacaggaaac agctatgacc                                                20

<210> SEQ ID NO 12
<211> LENGTH: 62
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(60)_Spacer18
```

```
<400> SEQUENCE: 12
tagacgggtc gacacgcgag cgaattctag actgcaggta acttactagg agcttttaat    60
gg                                                                  62

<210> SEQ ID NO 13
<211> LENGTH: 61
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(60)_Spacer18

<400> SEQUENCE: 13
tacgttccgg tagcacggtc cgaattctag actgccacaa tagagtgaaa tgtatgattg    60
g                                                                   61

<210> SEQ ID NO 14
<211> LENGTH: 57
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 14
tagacgggtc gacacgcgag cgaattctag actgcaggag actggcgggt agaaagg      57

<210> SEQ ID NO 15
<211> LENGTH: 58
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 15
tacgttccgg tagcacggtc cgaattctag actgccactt ccttcgcact cttaggat     58

<210> SEQ ID NO 16
<211> LENGTH: 60
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 16
tagacgggtc gacacgcgag cgaattctag actgcaggca tggtagttta gctggttgac    60

<210> SEQ ID NO 17
<211> LENGTH: 60
<212> TYPE: DNA
<213> ORGANISM: Artificial sequence
<220> FEATURE:
<223> OTHER INFORMATION: Synthetic sequence: Oligonucleotide
<220> FEATURE:
```

```
<221> NAME/KEY: misc_feature
<222> LOCATION: (1)..(1)
<223> OTHER INFORMATION: Linked to dT(50)_Spacer18

<400> SEQUENCE: 17
tacgttccgg tagcacggtc cgaattctag actgccacgc tctatttaaa gatggcaaga     60

<210> SEQ ID NO 18
<211> LENGTH: 56
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 18
tagacgggtc gacacgcgag cgaattctag actgcaggtt cccagggtct cctcca         56

<210> SEQ ID NO 19
<211> LENGTH: 57
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 19
tacgttccgg tagcacggtc cgaattctag actgccacgg cagctcttcc gttctct        57

<210> SEQ ID NO 20
<211> LENGTH: 60
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 20
tagacgggtc gacacgcgag cgaattctag actgcaggtt tatcaattcc tgctcaaaca     60

<210> SEQ ID NO 21
<211> LENGTH: 59
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 21
tacgttccgg tagcacggtc cgaattctag actgccacca aatcagcaat gatgggata      59

<210> SEQ ID NO 22
<211> LENGTH: 58
<212> TYPE: DNA
<213> ORGANISM: Artificial sequence
<220> FEATURE:
<223> OTHER INFORMATION: Synthetic sequence: Oligonucleotide
<220> FEATURE:
```

```
<221> NAME/KEY: misc_feature
<222> LOCATION: (1)..(1)
<223> OTHER INFORMATION: Linked to dT(50)_Spacer18

<400> SEQUENCE: 22
tagacgggtc gacacgcgag cgaattctag actgcaggag agctggcctg attcactt          58

<210> SEQ ID NO 23
<211> LENGTH: 59
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 23
tacgttccgg tagcacggtc cgaattctag actgccacac actcacaaga ccgatttcc         59

<210> SEQ ID NO 24
<211> LENGTH: 56
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 24
tagacgggtc gacacgcgag cgaattctag actgcagggc ggcccttgtt caagat            56

<210> SEQ ID NO 25
<211> LENGTH: 57
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 25
tacgttccgg tagcacggtc cgaattctag actgccacac gatagtcatg gggctgt           57

<210> SEQ ID NO 26
<211> LENGTH: 58
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 26
tagacgggtc gacacgcgag cgaattctag actgcaggag taagtcccca gcaaggtg         58

<210> SEQ ID NO 27
<211> LENGTH: 57
<212> TYPE: DNA
<213> ORGANISM: Artificial sequence
<220> FEATURE:
<223> OTHER INFORMATION: Synthetic sequence: Oligonucleotide
<220> FEATURE:
```

```
<221> NAME/KEY: misc_feature
<222> LOCATION: (1)..(1)
<223> OTHER INFORMATION: Linked to dT(50)_Spacer18

<400> SEQUENCE: 27
tacgttccgg tagcacggtc cgaattctag actgccacgg ggccaggtga tatgttc      57

<210> SEQ ID NO 28
<211> LENGTH: 60
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 28
tagacgggtc gacacgcgag cgaattctag actgcagggg cagtgtgtaa ggaagacaga   60

<210> SEQ ID NO 29
<211> LENGTH: 60
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 29
tacgttccgg tagcacggtc cgaattctag actgccacaa gggactccgt gtatgaagaa   60

<210> SEQ ID NO 30
<211> LENGTH: 58
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 30
tagacgggtc gacacgcgag cgaattctag actgcaggca ccctcccatg aacattat     58

<210> SEQ ID NO 31
<211> LENGTH: 57
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 31
tacgttccgg tagcacggtc cgaattctag actgccactg tgtgttgtgt tggatgc      57

<210> SEQ ID NO 32
<211> LENGTH: 57
<212> TYPE: DNA
<213> ORGANISM: Artificial sequence
<220> FEATURE:
<223> OTHER INFORMATION: Synthetic sequence: Oligonucleotide
<220> FEATURE:
```

```
<221> NAME/KEY: misc_feature
<222> LOCATION: (1)..(1)
<223> OTHER INFORMATION: Linked to dT(50)_Spacer18

<400> SEQUENCE: 32
tagacgggtc gacacgcgag cgaattctag actgcaggga gcaggaagaa cggaatg      57

<210> SEQ ID NO 33
<211> LENGTH: 57
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 33
tacgttccgg tagcacggtc cgaattctag actgccacat tctcgacggc tcacaag      57

<210> SEQ ID NO 34
<211> LENGTH: 61
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 34
tagacgggtc gacacgcgag cgaattctag actgcaggct ggattctgag gtcacttcta   60
c                                                                    61

<210> SEQ ID NO 35
<211> LENGTH: 59
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 35
tacgttccgg tagcacggtc cgaattctag actgccacca acacaaggct tttgcactt    59

<210> SEQ ID NO 36
<211> LENGTH: 59
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 36
tagacgggtc gacacgcgag cgaattctag actgcaggcc catcttaggt tctgggtct    59

<210> SEQ ID NO 37
<211> LENGTH: 59
<212> TYPE: DNA
<213> ORGANISM: Artificial sequence
<220> FEATURE:
```

<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 37
tacgttccgg tagcacggtc cgaattctag actgccactg agatattcct ttgggctct    59

<210> SEQ ID NO 38
<211> LENGTH: 57
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 38
tagacgggtc gacacgcgag cgaattctag actgcaggtt ggcaatgttg caagaac    57

<210> SEQ ID NO 39
<211> LENGTH: 59
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 39
tacgttccgg tagcacggtc cgaattctag actgccacca agcctcgtcg tactaatga    59

<210> SEQ ID NO 40
<211> LENGTH: 57
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 40
tagacgggtc gacacgcgag cgaattctag actgcaggcc tgcaccagtt tccatcc    57

<210> SEQ ID NO 41
<211> LENGTH: 57
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 41
tacgttccgg tagcacggtc cgaattctag actgccacag tctggcaggt cggttct    57

<210> SEQ ID NO 42
<211> LENGTH: 59
<212> TYPE: DNA
<213> ORGANISM: Artificial sequence
<220> FEATURE:

```
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 42
tagacgggtc gacacgcgag cgaattctag actgcagggc catcgatgtt gactttaga        59

<210> SEQ ID NO 43
<211> LENGTH: 59
<212> TYPE: DNA
<213> ORGANISM: Artificial sequence
<220> FEATURE:
<223> OTHER INFORMATION: Synthetic sequence: Oligonucleotide
<220> FEATURE:
<221> NAME/KEY: misc_feature
<222> LOCATION: (1)..(1)
<223> OTHER INFORMATION: Linked to dT(50)_Spacer18

<400> SEQUENCE: 43
tacgttccgg tagcacggtc cgaattctag actgccacaa acagctgaca aacattgga        59

<210> SEQ ID NO 44
<211> LENGTH: 40
<212> TYPE: DNA
<213> ORGANISM: Artificial sequence
<220> FEATURE:
<223> OTHER INFORMATION: Synthetic sequence: Oligonucleotide

<400> SEQUENCE: 44
actggccgtc gttttacaac ctgcagtcta gaattcgctc                              40

<210> SEQ ID NO 45
<211> LENGTH: 38
<212> TYPE: DNA
<213> ORGANISM: Artificial sequence
<220> FEATURE:
<223> OTHER INFORMATION: Synthetic sequence: Oligonucleotide

<400> SEQUENCE: 45
ggtcatagct gttcctgtg gcagtctaga attcggac                                 38

<210> SEQ ID NO 46
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 46
gatgaatgca acataagtct at                                                 22

<210> SEQ ID NO 47
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 47
agtattttcc tggtattagg gg                                                 22

<210> SEQ ID NO 48
<211> LENGTH: 22
<212> TYPE: DNA
<213> ORGANISM: Artificial sequence
<220> FEATURE:
```

<223> OTHER INFORMATION: Synthetic sequence: Oligonucleotide

<400> SEQUENCE: 48
gtcacaagct tattacatcc ta                                              22

<210> SEQ ID NO 49
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 49
aattatatga tgtggtgtct cc                                              22

<210> SEQ ID NO 50
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 50
aaccctagga tattactgag ga                                              22

<210> SEQ ID NO 51
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 51
taacaatttc tgtccttcag at                                              22

<210> SEQ ID NO 52
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 52
ctggtcaaag aagatagaga ct                                              22

<210> SEQ ID NO 53
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 53
gggttagaga aatgtgtaac aa                                              22

<210> SEQ ID NO 54
<211> LENGTH: 23
<212> TYPE: DNA
<213> ORGANISM: Artificial sequence
<220> FEATURE:
<223> OTHER INFORMATION: Synthetic sequence: Oligonucleotide

<400> SEQUENCE: 54
gctgtagttt tcatcttact tct                                             23

<210> SEQ ID NO 55

-continued

```
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 55
cctaaagttt aaagtgcttt cc                                              22

<210> SEQ ID NO 56
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 56
ttttcaggga atgtatctta gg                                              22

<210> SEQ ID NO 57
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 57
tatcacaggt cttttggttt tt                                              22

<210> SEQ ID NO 58
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 58
gtgttaggag agaggagata cc                                              22

<210> SEQ ID NO 59
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 59
gaagtaggga aaacactggt tg                                              22

<210> SEQ ID NO 60
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 60
tgttccaaaa agagatctat gg                                              22

<210> SEQ ID NO 61
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 61
```

```
atcaaacacc atacaaaaac ca                                              22

<210> SEQ ID NO 62
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 62
aactacacat cttgatcagc tt                                              22

<210> SEQ ID NO 63
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 63
aaagtcatta ggtgagcaaa aa                                              22

<210> SEQ ID NO 64
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 64
aagataattt ggtgatccaa cc                                              22

<210> SEQ ID NO 65
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 65
acgtgagtac tttctctcct tt                                              22

<210> SEQ ID NO 66
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 66
ctttcaacat cctagctcca ac                                              22

<210> SEQ ID NO 67
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 67
atgcatttac cttcccagat gt                                              22

<210> SEQ ID NO 68
<211> LENGTH: 22
<212> TYPE: DNA
<213> ORGANISM: Artificial sequence
<220> FEATURE:
```

<223> OTHER INFORMATION: Synthetic sequence: Oligonucleotide

<400> SEQUENCE: 68
cttagcttct caccaaaatg aa          22

<210> SEQ ID NO 69
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 69
ttaacaagaa ccatgccatt tt          22

<210> SEQ ID NO 70
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 70
tccattgctt ctccagatca aa          22

<210> SEQ ID NO 71
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 71
agatgagctg ctgataagtt ct          22

<210> SEQ ID NO 72
<211> LENGTH: 23
<212> TYPE: DNA
<213> ORGANISM: Artificial sequence
<220> FEATURE:
<223> OTHER INFORMATION: Synthetic sequence: Oligonucleotide

<400> SEQUENCE: 72
gggagtaggg tacaatacag tct          23

<210> SEQ ID NO 73
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 73
ctttcccacc aaggtcacaa aa          22

<210> SEQ ID NO 74
<211> LENGTH: 25
<212> TYPE: DNA
<213> ORGANISM: Artificial sequence
<220> FEATURE:
<223> OTHER INFORMATION: Synthetic sequence: Oligonucleotide

<400> SEQUENCE: 74
cctccttcat tagatccatt aattt          25

<210> SEQ ID NO 75

```
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 75
ttttggttct gaactcatcc at                                                  22

<210> SEQ ID NO 76
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 76
catgcatgtc ccaccacaat ta                                                  22

<210> SEQ ID NO 77
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 77
tttcctacta tgcccaaacc ca                                                  22

<210> SEQ ID NO 78
<211> LENGTH: 25
<212> TYPE: DNA
<213> ORGANISM: Artificial sequence
<220> FEATURE:
<223> OTHER INFORMATION: Synthetic sequence: Oligonucleotide

<400> SEQUENCE: 78
aaagagagag agagaatttt agcat                                               25

<210> SEQ ID NO 79
<211> LENGTH: 25
<212> TYPE: DNA
<213> ORGANISM: Artificial sequence
<220> FEATURE:
<223> OTHER INFORMATION: Synthetic sequence: Oligonucleotide

<400> SEQUENCE: 79
ttaccttgag aagtttagag gtgat                                               25

<210> SEQ ID NO 80
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 80
gggtccaagt aggcaaagag ac                                                  22

<210> SEQ ID NO 81
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 81
```

```
ctggaatcac acctcccca ta                                              22

<210> SEQ ID NO 82
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 82
taagccacac tgatgccttg ac                                             22

<210> SEQ ID NO 83
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 83
catggaggct ttagatggct ca                                             22

<210> SEQ ID NO 84
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 84
acggtctctt ttgttcactg gc                                             22

<210> SEQ ID NO 85
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 85
tctcagttcc cactaggcca aa                                             22

<210> SEQ ID NO 86
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 86
cagcttccaa ggagaagact gc                                             22

<210> SEQ ID NO 87
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 87
ccgcagaaat gcttcttccg tt                                             22

<210> SEQ ID NO 88
<211> LENGTH: 22
<212> TYPE: DNA
<213> ORGANISM: Artificial sequence
<220> FEATURE:
```

<223> OTHER INFORMATION: Synthetic sequence: Oligonucleotide

<400> SEQUENCE: 88
gttgacccag agatccccca gg                                    22

<210> SEQ ID NO 89
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 89
caagtgagtt gccctgactg cc                                    22

<210> SEQ ID NO 90
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 90
gtactggagg cccccattgt gc                                    22

<210> SEQ ID NO 91
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 91
aagacctaca tcgccagcca gg                                    22

<210> SEQ ID NO 92
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 92
cagtcctact gtgggtgcct gc                                    22

<210> SEQ ID NO 93
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 93
ccatctcact cctagcttat tc                                    22

<210> SEQ ID NO 94
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 94
catcagcctc tctttaaaat gt                                    22

<210> SEQ ID NO 95

```
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 95
cccctagaga aacgatagac tg                                        22

<210> SEQ ID NO 96
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 96
tgcttccaca cacaaatgta at                                        22

<210> SEQ ID NO 97
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 97
gaactctgtt acatgcctca tt                                        22

<210> SEQ ID NO 98
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 98
tactttaggg atgagtggga ac                                        22

<210> SEQ ID NO 99
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 99
agggatgaag agaaaaccag ac                                        22

<210> SEQ ID NO 100
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 100
atttcactaa aaccatccct aa                                        22

<210> SEQ ID NO 101
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 101
```

```
ataggcatac aactttctg ag                                             22

<210> SEQ ID NO 102
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 102
agtctggcac aggtgtcttc ag                                            22

<210> SEQ ID NO 103
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 103
aggacattat gaggtattca aa                                            22

<210> SEQ ID NO 104
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 104
acaacttgca ataaaacaga ca                                            22

<210> SEQ ID NO 105
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 105
taaatgtctc ccctcacgta ca                                            22

<210> SEQ ID NO 106
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 106
aacctctgca tttattgtca gc                                            22

<210> SEQ ID NO 107
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 107
cagttacagc catcagaaaa ct                                            22

<210> SEQ ID NO 108
<211> LENGTH: 22
<212> TYPE: DNA
<213> ORGANISM: Artificial sequence
<220> FEATURE:
```

<223> OTHER INFORMATION: Synthetic sequence: Oligonucleotide

<400> SEQUENCE: 108
gggtttacat aaacttctgc cc                                              22

<210> SEQ ID NO 109
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 109
cacctgtggg aaatgaagga aa                                              22

<210> SEQ ID NO 110
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 110
gtaaaatctg caactcttcc tt                                              22

<210> SEQ ID NO 111
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 111
gtttgattca ttcgagacaa ca                                              22

<210> SEQ ID NO 112
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 112
agaggaaata atccaggcaa gg                                              22

<210> SEQ ID NO 113
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 113
gccatataca atctttgagt ag                                              22

<210> SEQ ID NO 114
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 114
gaggaaagtt tacagaaaca gt                                              22

<210> SEQ ID NO 115

```
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 115
taattccatc tgcttctttg aa                                              22

<210> SEQ ID NO 116
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 116
gcagggccac agcaggttag ac                                              22

<210> SEQ ID NO 117
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 117
agagaacttc cagtctattt gc                                              22

<210> SEQ ID NO 118
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 118
agagtggaag acaccgttgt aa                                              22

<210> SEQ ID NO 119
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 119
cccgctacag atgaaacagg ta                                              22

<210> SEQ ID NO 120
<211> LENGTH: 25
<212> TYPE: DNA
<213> ORGANISM: Artificial sequence
<220> FEATURE:
<223> OTHER INFORMATION: Synthetic sequence: Oligonucleotide

<400> SEQUENCE: 120
ggtgtaggag atatgtacag tcaat                                           25

<210> SEQ ID NO 121
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 121
```

-continued agcctaagtt agtgtcccca ag                                              22

<210> SEQ ID NO 122
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 122
cagaaagaag gagctggagg ag                                              22

<210> SEQ ID NO 123
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 123
ggttgaatta gttgaccctg ac                                              22

<210> SEQ ID NO 124
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 124
cagacaggca gtgagcagag gg                                              22

<210> SEQ ID NO 125
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 125
gtagtagcaa tttgtttggt ga                                              22

<210> SEQ ID NO 126
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 126
tctttgatac acggcaaggt gc                                              22

<210> SEQ ID NO 127
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 127
ccaaaaaggg tttctatttt ag                                              22

<210> SEQ ID NO 128
<211> LENGTH: 23
<212> TYPE: DNA
<213> ORGANISM: Artificial sequence
<220> FEATURE:

```
<223> OTHER INFORMATION: Synthetic sequence: Oligonucleotide

<400> SEQUENCE: 128
taacaagtcc gtagggtttc cat                                            23

<210> SEQ ID NO 129
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 129
aattctggct ggagatggga ag                                             22

<210> SEQ ID NO 130
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 130
acatttatgg gctctgctct ta                                             22

<210> SEQ ID NO 131
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 131
gatgcttcca atttagagac aa                                             22

<210> SEQ ID NO 132
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 132
gaataggccc ctctctctgg tc                                             22

<210> SEQ ID NO 133
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 133
gtgagtgttt cagaacgata ga                                             22

<210> SEQ ID NO 134
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 134
aagtcagatc ttgctctatg tg                                             22

<210> SEQ ID NO 135
```

```
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 135
gggaaggata tcgcatctta aa                                           22

<210> SEQ ID NO 136
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 136
tggggaatcc ggtattactt tt                                           22

<210> SEQ ID NO 137
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 137
tctcatctgg ggaaagactg tg                                           22

<210> SEQ ID NO 138
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 138
agacagcttg gtggggatac ac                                           22

<210> SEQ ID NO 139
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 139
ggacaaaggg gtggatgccg gg                                           22

<210> SEQ ID NO 140
<211> LENGTH: 25
<212> TYPE: DNA
<213> ORGANISM: Artificial sequence
<220> FEATURE:
<223> OTHER INFORMATION: Synthetic sequence: Oligonucleotide

<400> SEQUENCE: 140
ccggataaaa attaagagag actca                                        25

<210> SEQ ID NO 141
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 141
```
tcattgaccg tggcctcaag ac                                              22

<210> SEQ ID NO 142
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 142
gcccaagcta gtcaggtcaa gg                                              22

<210> SEQ ID NO 143
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 143
tctttgagga ggaaatatgt tg                                              22

<210> SEQ ID NO 144
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 144
gtaaggggct tcaaaggaat gc                                              22

<210> SEQ ID NO 145
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 145
ttgaggtgag ggattaaaca at                                              22

<210> SEQ ID NO 146
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 146
tttttttttt gagcgaattc tagactgcag gttgtaaaac gacggccagt gatgaatgca     60
acataagtct at                                                         72

<210> SEQ ID NO 147
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 147
tttttttttt gtccgaattc tagactgcca caggaaacag ctatgacctg cttccacaca     60
caaatgtaat                                                            70

<210> SEQ ID NO 148

```
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 148
tttttttttt gagcgaattc tagactgcag gttgtaaaac gacggccagt agtattttcc      60
tggtattagg gg                                                          72

<210> SEQ ID NO 149
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 149
tttttttttt gtccgaattc tagactgcca caggaaacag ctatgaccga actctgttac      60
atgcctcatt                                                             70

<210> SEQ ID NO 150
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 150
tttttttttt gagcgaattc tagactgcag gttgtaaaac gacggccagt gtcacaagct      60
tattacatcc ta                                                          72

<210> SEQ ID NO 151
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 151
tttttttttt gtccgaattc tagactgcca caggaaacag ctatgaccta ctttagggat      60
gagtgggaac                                                             70

<210> SEQ ID NO 152
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 152
tttttttttt gagcgaattc tagactgcag gttgtaaaac gacggccagt aattatatga      60
tgtggtgtct cc                                                          72

<210> SEQ ID NO 153
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 153
tttttttttt gtccgaattc tagactgcca caggaaacag ctatgaccag ggatgaagag      60
```
aaaaccagac                                                              70

<210> SEQ ID NO 154
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 154
tttttttttt gagcgaattc tagactgcag gttgtaaaac gacggccagt aaccctagga      60
tattactgag ga                                                           72

<210> SEQ ID NO 155
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 155
tttttttttt gtccgaattc tagactgcca caggaaacag ctatgaccat ttcactaaaa      60
ccatccctaa                                                              70

<210> SEQ ID NO 156
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 156
tttttttttt gagcgaattc tagactgcag gttgtaaaac gacggccagt taacaatttc      60
tgtccttcag at                                                           72

<210> SEQ ID NO 157
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 157
tttttttttt gtccgaattc tagactgcca caggaaacag ctatgaccat aggcatacaa      60
cttttctgag                                                              70

<210> SEQ ID NO 158
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 158
tttttttttt gagcgaattc tagactgcag gttgtaaaac gacggccagt ctggtcaaag      60
aagatagaga ct                                                           72

<210> SEQ ID NO 159
<211> LENGTH: 70
<212> TYPE: DNA
<213> ORGANISM: Artificial sequence
<220> FEATURE:
<223> OTHER INFORMATION: Synthetic sequence: Oligonucleotide -continued

```
<400> SEQUENCE: 159
tttttttttt gtccgaattc tagactgcca caggaaacag ctatgaccag tctggcacag    60
gtgtcttcag                                                           70

<210> SEQ ID NO 160
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 160
tttttttttt gagcgaattc tagactgcag gttgtaaaac gacggccagt gggttagaga    60
aatgtgtaac aa                                                        72

<210> SEQ ID NO 161
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 161
tttttttttt gtccgaattc tagactgcca caggaaacag ctatgaccag gacattatga    60
ggtattcaaa                                                           70

<210> SEQ ID NO 162
<211> LENGTH: 73
<212> TYPE: DNA
<213> ORGANISM: Artificial sequence
<220> FEATURE:
<223> OTHER INFORMATION: Synthetic sequence: Oligonucleotide

<400> SEQUENCE: 162
tttttttttt gagcgaattc tagactgcag gttgtaaaac gacggccagt gctgtagttt    60
tcatcttact tct                                                       73

<210> SEQ ID NO 163
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 163
tttttttttt gtccgaattc tagactgcca caggaaacag ctatgaccac aacttgcaat    60
aaaacagaca                                                           70

<210> SEQ ID NO 164
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 164
tttttttttt gagcgaattc tagactgcag gttgtaaaac gacggccagt cctaaagttt    60
aaagtgcttt cc                                                        72

<210> SEQ ID NO 165
<211> LENGTH: 70
<212> TYPE: DNA
```

<213> ORGANISM: Artificial sequence
<220> FEATURE:
<223> OTHER INFORMATION: Synthetic sequence: Oligonucleotide

<400> SEQUENCE: 165 ttttttttt gtccgaattc tagactgcca caggaaacag ctatgaccta aatgtctccc    60
ctcacgtaca    70

<210> SEQ ID NO 166
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 166 ttttttttt gagcgaattc tagactgcag gttgtaaaac gacggccagt ttttcaggga    60
atgtatctta gg    72

<210> SEQ ID NO 167
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 167 ttttttttt gtccgaattc tagactgcca caggaaacag ctatgaccaa cctctgcatt    60
tattgtcagc    70

<210> SEQ ID NO 168
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 168 ttttttttt gagcgaattc tagactgcag gttgtaaaac gacggccagt tatcacaggt    60
cttttggttt tt    72

<210> SEQ ID NO 169
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 169 ttttttttt gtccgaattc tagactgcca caggaaacag ctatgaccca gttacagcca    60
tcagaaaact    70

<210> SEQ ID NO 170
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 170 ttttttttt gagcgaattc tagactgcag gttgtaaaac gacggccagt gtgttaggag    60
agaggagata cc    72

<210> SEQ ID NO 171
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 171
tttttttttt gtccgaattc tagactgcca caggaaacag ctatgaccgg gtttacataa    60
acttctgccc                                                          70

<210> SEQ ID NO 172
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 172
tttttttttt gagcgaattc tagactgcag gttgtaaaac gacggccagt gaagtaggga    60
aaacactggt tg                                                       72

<210> SEQ ID NO 173
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 173
tttttttttt gtccgaattc tagactgcca caggaaacag ctatgaccca cctgtgggaa    60
atgaaggaaa                                                          70

<210> SEQ ID NO 174
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 174
tttttttttt gagcgaattc tagactgcag gttgtaaaac gacggccagt tgttccaaaa    60
agagatctat gg                                                       72

<210> SEQ ID NO 175
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 175
tttttttttt gtccgaattc tagactgcca caggaaacag ctatgaccgt aaaatctgca    60
actcttcctt                                                          70

<210> SEQ ID NO 176
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 176

```
tttttttttt gagcgaattc tagactgcag gttgtaaaac gacggccagt atcaaacacc    60
atacaaaaac ca                                                        72

<210> SEQ ID NO 177
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 177
tttttttttt gtccgaattc tagactgcca caggaaacag ctatgaccgt ttgattcatt    60
cgagacaaca                                                           70

<210> SEQ ID NO 178
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 178
tttttttttt gagcgaattc tagactgcag gttgtaaaac gacggccagt aactacacat    60
cttgatcagc tt                                                        72

<210> SEQ ID NO 179
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 179
tttttttttt gtccgaattc tagactgcca caggaaacag ctatgaccag aggaaataat    60
ccaggcaagg                                                           70

<210> SEQ ID NO 180
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 180
tttttttttt gagcgaattc tagactgcag gttgtaaaac gacggccagt aaagtcatta    60
ggtgagcaaa aa                                                        72

<210> SEQ ID NO 181
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 181
tttttttttt gtccgaattc tagactgcca caggaaacag ctatgaccgc catatacaat    60
ctttgagtag                                                           70

<210> SEQ ID NO 182
<211> LENGTH: 72
<212> TYPE: DNA
<213> ORGANISM: Artificial sequence
<220> FEATURE:
```

<223> OTHER INFORMATION: Synthetic sequence: Oligonucleotide

<400> SEQUENCE: 182
tttttttttt gagcgaattc tagactgcag gttgtaaaac gacggccagt aagataattt    60
ggtgatccaa cc    72

<210> SEQ ID NO 183
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 183
tttttttttt gtccgaattc tagactgcca caggaaacag ctatgaccga ggaaagttta    60
cagaaacagt    70

<210> SEQ ID NO 184
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 184
tttttttttt gagcgaattc tagactgcag gttgtaaaac gacggccagt acgtgagtac    60
tttctctcct tt    72

<210> SEQ ID NO 185
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 185
tttttttttt gtccgaattc tagactgcca caggaaacag ctatgaccta attccatctg    60
cttctttgaa    70

<210> SEQ ID NO 186
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 186
tttttttttt gagcgaattc tagactgcag gttgtaaaac gacggccagt ctttcaacat    60
cctagctcca ac    72

<210> SEQ ID NO 187
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 187
tttttttttt gtccgaattc tagactgcca caggaaacag ctatgaccgc agggccacag    60
caggttagac    70

<210> SEQ ID NO 188

```
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 188
tttttttttt gagcgaattc tagactgcag gttgtaaaac gacggccagt atgcatttac    60
cttcccagat gt                                                         72

<210> SEQ ID NO 189
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 189
tttttttttt gtccgaattc tagactgcca caggaaacag ctatgaccag agaacttcca    60
gtctatttgc                                                            70

<210> SEQ ID NO 190
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 190
tttttttttt gagcgaattc tagactgcag gttgtaaaac gacggccagt cttagcttct    60
caccaaaatg aa                                                         72

<210> SEQ ID NO 191
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 191
tttttttttt gtccgaattc tagactgcca caggaaacag ctatgaccag agtggaagac    60
accgttgtaa                                                            70

<210> SEQ ID NO 192
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 192
tttttttttt gagcgaattc tagactgcag gttgtaaaac gacggccagt ttaacaagaa    60
ccatgccatt tt                                                         72

<210> SEQ ID NO 193
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 193
tttttttttt gtccgaattc tagactgcca caggaaacag ctatgacccc cgctacagat    60
```

| gaaacaggta | 70 |

<210> SEQ ID NO 194
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 194

| tttttttttt gagcgaattc tagactgcag gttgtaaaac gacggccagt tccattgctt | 60 |
| ctccagatca aa | 72 |

<210> SEQ ID NO 195
<211> LENGTH: 73
<212> TYPE: DNA
<213> ORGANISM: Artificial sequence
<220> FEATURE:
<223> OTHER INFORMATION: Synthetic sequence: Oligonucleotide

<400> SEQUENCE: 195

| tttttttttt gtccgaattc tagactgcca caggaaacag ctatgaccgg tgtaggagat | 60 |
| atgtacagtc aat | 73 |

<210> SEQ ID NO 196
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 196

| tttttttttt gagcgaattc tagactgcag gttgtaaaac gacggccagt agatgagctg | 60 |
| ctgataagtt ct | 72 |

<210> SEQ ID NO 197
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 197

| tttttttttt gtccgaattc tagactgcca caggaaacag ctatgaccag cctaagttag | 60 |
| tgtccccaag | 70 |

<210> SEQ ID NO 198
<211> LENGTH: 73
<212> TYPE: DNA
<213> ORGANISM: Artificial sequence
<220> FEATURE:
<223> OTHER INFORMATION: Synthetic sequence: Oligonucleotide

<400> SEQUENCE: 198

| tttttttttt gagcgaattc tagactgcag gttgtaaaac gacggccagt gggagtaggg | 60 |
| tacaatacag tct | 73 |

<210> SEQ ID NO 199
<211> LENGTH: 70
<212> TYPE: DNA
<213> ORGANISM: Artificial sequence
<220> FEATURE:
<223> OTHER INFORMATION: Synthetic sequence: Oligonucleotide -continued

<400> SEQUENCE: 199
tttttttttt gtccgaattc tagactgcca caggaaacag ctatgaccca gaaagaagga    60
gctggaggag                                                          70

<210> SEQ ID NO 200
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 200
tttttttttt gagcgaattc tagactgcag gttgtaaaac gacggccagt ctttcccacc    60
aaggtcacaa aa                                                       72

<210> SEQ ID NO 201
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 201
tttttttttt gtccgaattc tagactgcca caggaaacag ctatgaccgg ttgaattagt    60
tgaccctgac                                                          70

<210> SEQ ID NO 202
<211> LENGTH: 75
<212> TYPE: DNA
<213> ORGANISM: Artificial sequence
<220> FEATURE:
<223> OTHER INFORMATION: Synthetic sequence: Oligonucleotide

<400> SEQUENCE: 202
tttttttttt gagcgaattc tagactgcag gttgtaaaac gacggccagt cctccttcat    60
tagatccatt aattt                                                    75

<210> SEQ ID NO 203
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 203
tttttttttt gtccgaattc tagactgcca caggaaacag ctatgaccca gacaggcagt    60
gagcagaggg                                                          70

<210> SEQ ID NO 204
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 204
tttttttttt gagcgaattc tagactgcag gttgtaaaac gacggccagt ttttggttct    60
gaactcatcc at                                                       72

<210> SEQ ID NO 205
<211> LENGTH: 70
<212> TYPE: DNA

```
<213> ORGANISM: Artificial sequence
<220> FEATURE:
<223> OTHER INFORMATION: Synthetic sequence: Oligonucleotide

<400> SEQUENCE: 205
tttttttttt gtccgaattc tagactgcca caggaaacag ctatgaccgt agtagcaatt    60
tgtttggtga                                                          70

<210> SEQ ID NO 206
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 206
tttttttttt gagcgaattc tagactgcag gttgtaaaac gacggccagt catgcatgtc    60
ccaccacaat ta                                                       72

<210> SEQ ID NO 207
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 207
tttttttttt gtccgaattc tagactgcca caggaaacag ctatgacctc tttgatacac    60
ggcaaggtgc                                                          70

<210> SEQ ID NO 208
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 208
tttttttttt gagcgaattc tagactgcag gttgtaaaac gacggccagt tttcctacta    60
tgcccaaacc ca                                                       72

<210> SEQ ID NO 209
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 209
tttttttttt gtccgaattc tagactgcca caggaaacag ctatgacccc aaaaagggtt    60
tctattttag                                                          70

<210> SEQ ID NO 210
<211> LENGTH: 75
<212> TYPE: DNA
<213> ORGANISM: Artificial sequence
<220> FEATURE:
<223> OTHER INFORMATION: Synthetic sequence: Oligonucleotide

<400> SEQUENCE: 210
tttttttttt gagcgaattc tagactgcag gttgtaaaac gacggccagt aaagagagag    60
agagaatttt agcat                                                    75
```

```
<210> SEQ ID NO 211
<211> LENGTH: 71
<212> TYPE: DNA
<213> ORGANISM: Artificial sequence
<220> FEATURE:
<223> OTHER INFORMATION: Synthetic sequence: Oligonucleotide

<400> SEQUENCE: 211
tttttttttt gtccgaattc tagactgcca caggaaacag ctatgaccta acaagtccgt    60
agggtttcca t                                                        71

<210> SEQ ID NO 212
<211> LENGTH: 75
<212> TYPE: DNA
<213> ORGANISM: Artificial sequence
<220> FEATURE:
<223> OTHER INFORMATION: Synthetic sequence: Oligonucleotide

<400> SEQUENCE: 212
tttttttttt gagcgaattc tagactgcag gttgtaaaac gacggccagt ttaccttgag    60
aagtttagag gtgat                                                    75

<210> SEQ ID NO 213
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 213
tttttttttt gtccgaattc tagactgcca caggaaacag ctatgaccaa ttctggctgg    60
agatgggaag                                                          70

<210> SEQ ID NO 214
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 214
tttttttttt gagcgaattc tagactgcag gttgtaaaac gacggccagt gggtccaagt    60
aggcaaagag ac                                                       72

<210> SEQ ID NO 215
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 215
tttttttttt gtccgaattc tagactgcca caggaaacag ctatgaccac atttatgggc    60
tctgctctta                                                          70

<210> SEQ ID NO 216
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 216
```

```
tttttttttt gagcgaattc tagactgcag gttgtaaaac gacggccagt ctggaatcac    60
acctccccca ta                                                       72

<210> SEQ ID NO 217
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 217
tttttttttt gtccgaattc tagactgcca caggaaacag ctatgaccga tgcttccaat    60
ttagagacaa                                                          70

<210> SEQ ID NO 218
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 218
tttttttttt gagcgaattc tagactgcag gttgtaaaac gacggccagt taagccacac    60
tgatgccttg ac                                                       72

<210> SEQ ID NO 219
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 219
tttttttttt gtccgaattc tagactgcca caggaaacag ctatgaccga ataggcccct    60
ctctctggtc                                                          70

<210> SEQ ID NO 220
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 220
tttttttttt gagcgaattc tagactgcag gttgtaaaac gacggccagt catggaggct    60
ttagatggct ca                                                       72

<210> SEQ ID NO 221
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 221
tttttttttt gtccgaattc tagactgcca caggaaacag ctatgaccgt gagtgtttca    60
gaacgataga                                                          70

<210> SEQ ID NO 222
<211> LENGTH: 72
<212> TYPE: DNA
<213> ORGANISM: Artificial sequence
<220> FEATURE:
```

<223> OTHER INFORMATION: Synthetic sequence: Oligonucleotide

<400> SEQUENCE: 222
tttttttttt gagcgaattc tagactgcag gttgtaaaac gacggccagt acggtctctt    60
ttgttcactg gc    72

<210> SEQ ID NO 223
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 223
tttttttttt gtccgaattc tagactgcca caggaaacag ctatgaccaa gtcagatctt    60
gctctatgtg    70

<210> SEQ ID NO 224
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 224
tttttttttt gagcgaattc tagactgcag gttgtaaaac gacggccagt tctcagttcc    60
cactaggcca aa    72

<210> SEQ ID NO 225
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 225
tttttttttt gtccgaattc tagactgcca caggaaacag ctatgaccgg gaaggatatc    60
gcatcttaaa    70

<210> SEQ ID NO 226
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 226
tttttttttt gagcgaattc tagactgcag gttgtaaaac gacggccagt cagcttccaa    60
ggagaagact gc    72

<210> SEQ ID NO 227
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 227
tttttttttt gtccgaattc tagactgcca caggaaacag ctatgacctg gggaatccgg    60
tattactttt    70

<210> SEQ ID NO 228

```
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 228 ttttttttttt gagcgaattc tagactgcag gttgtaaaac gacggccagt ccgcagaaat    60
gcttcttccg tt                                                        72

<210> SEQ ID NO 229
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 229 ttttttttttt gtccgaattc tagactgcca caggaaacag ctatgacctc tcatctgggg    60
aaagactgtg                                                           70

<210> SEQ ID NO 230
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 230 ttttttttttt gagcgaattc tagactgcag gttgtaaaac gacggccagt gttgacccag    60
agatccccca gg                                                        72

<210> SEQ ID NO 231
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 231 ttttttttttt gtccgaattc tagactgcca caggaaacag ctatgaccag acagcttggt    60
ggggatacac                                                           70

<210> SEQ ID NO 232
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 232 ttttttttttt gagcgaattc tagactgcag gttgtaaaac gacggccagt caagtgagtt    60
gccctgactg cc                                                        72

<210> SEQ ID NO 233
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 233 ttttttttttt gtccgaattc tagactgcca caggaaacag ctatgaccgg acaaagggt    60
```
ggatgccggg 70

<210> SEQ ID NO 234
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 234
tttttttttt gagcgaattc tagactgcag gttgtaaaac gacggccagt gtactggagg    60
cccccattgt gc    72

<210> SEQ ID NO 235
<211> LENGTH: 73
<212> TYPE: DNA
<213> ORGANISM: Artificial sequence
<220> FEATURE:
<223> OTHER INFORMATION: Synthetic sequence: Oligonucleotide

<400> SEQUENCE: 235
tttttttttt gtccgaattc tagactgcca caggaaacag ctatgacccc ggataaaaat    60
taagagagac tca    73

<210> SEQ ID NO 236
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 236
tttttttttt gagcgaattc tagactgcag gttgtaaaac gacggccagt aagacctaca    60
tcgccagcca gg    72

<210> SEQ ID NO 237
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 237
tttttttttt gtccgaattc tagactgcca caggaaacag ctatgacctc attgaccgtg    60
gcctcaagac    70

<210> SEQ ID NO 238
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 238
tttttttttt gagcgaattc tagactgcag gttgtaaaac gacggccagt cagtcctact    60
gtgggtgcct gc    72

<210> SEQ ID NO 239
<211> LENGTH: 70
<212> TYPE: DNA
<213> ORGANISM: Artificial sequence
<220> FEATURE:
<223> OTHER INFORMATION: Synthetic sequence: Oligonucleotide -continued

```
<400> SEQUENCE: 239
tttttttttt gtccgaattc tagactgcca caggaaacag ctatgaccgc ccaagctagt      60
caggtcaagg                                                            70

<210> SEQ ID NO 240
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 240
tttttttttt gagcgaattc tagactgcag gttgtaaaac gacggccagt ccatctcact     60
cctagcttat tc                                                         72

<210> SEQ ID NO 241
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 241
tttttttttt gtccgaattc tagactgcca caggaaacag ctatgacctc tttgaggagg     60
aaatatgttg                                                            70

<210> SEQ ID NO 242
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 242
tttttttttt gagcgaattc tagactgcag gttgtaaaac gacggccagt catcagcctc     60
tctttaaaat gt                                                         72

<210> SEQ ID NO 243
<211> LENGTH: 70
<212> TYPE: DNA
<213> ORGANISM: Artificial sequence
<220> FEATURE:
<223> OTHER INFORMATION: Synthetic sequence: Oligonucleotide

<400> SEQUENCE: 243
tttttttttt gtccgaattc tagactgcca caggaaacag ctatgaccgt aaggggcttc     60
aaaggaatgc                                                            70

<210> SEQ ID NO 244
<211> LENGTH: 72
<212> TYPE: DNA
<213> ORGANISM: Artificial sequence
<220> FEATURE:
<223> OTHER INFORMATION: Synthetic sequence: Oligonucleotide

<400> SEQUENCE: 244
tttttttttt gagcgaattc tagactgcag gttgtaaaac gacggccagt cccctagaga     60
aacgatagac tg                                                         72

<210> SEQ ID NO 245
<211> LENGTH: 70
<212> TYPE: DNA
```

```
<213> ORGANISM: Artificial sequence
<220> FEATURE:
<223> OTHER INFORMATION: Synthetic sequence: Oligonucleotide

<400> SEQUENCE: 245
tttttttttt gtccgaattc tagactgcca caggaaacag ctatgacctt gaggtgaggg      60
attaaacaat                                                            70

<210> SEQ ID NO 246
<211> LENGTH: 60
<212> TYPE: DNA
<213> ORGANISM: Artificial sequence
<220> FEATURE:
<223> OTHER INFORMATION: Synthetic sequence: Oligonucleotide

<400> SEQUENCE: 246
tttttttttt tttttttttt tttttttttt tttttttttt tttttttttt tttttttttt      60

<210> SEQ ID NO 247
<211> LENGTH: 50
<212> TYPE: DNA
<213> ORGANISM: Artificial sequence
<220> FEATURE:
<223> OTHER INFORMATION: Synthetic sequence: Oligonucleotide

<400> SEQUENCE: 247
tttttttttt tttttttttt tttttttttt tttttttttt tttttttttt                50
```